(12) United States Patent
Curran et al.

(10) Patent No.: US 8,187,334 B2
(45) Date of Patent: May 29, 2012

(54) SYSTEM AND METHODS FOR SPINAL FUSION

(75) Inventors: Matthew Curran, Carlsbad, CA (US); Mark Peterson, Medford, OR (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/079,645

(22) Filed: Apr. 4, 2011

(65) Prior Publication Data

US 2012/0029641 A1    Feb. 2, 2012

Related U.S. Application Data

(63) Continuation of application No. 11/093,409, filed on Mar. 29, 2005, now Pat. No. 7,918,891.

(60) Provisional application No. 60/557,536, filed on Mar. 29, 2004.

(51) Int. Cl.
    *A61F 2/44*   (2006.01)
(52) U.S. Cl. .................................................. 623/17.16
(58) Field of Classification Search ..... 623/17.11–17.16
    See application file for complete search history.

(56) References Cited

U.S. PATENT DOCUMENTS

| | | | |
|---|---|---|---|
| 3,486,505 A | 12/1969 | Morrison | |
| 3,518,993 A | 7/1970 | Blake | |
| 3,604,487 A | 9/1971 | Gilbert | |
| 3,745,995 A | 7/1973 | Kraus | |
| 3,848,601 A | 11/1974 | Ma et al. | |
| 3,867,728 A | 2/1975 | Stubstad et al. | |
| 4,026,304 A | 5/1977 | Levy | |
| 4,026,305 A | 5/1977 | Brownlee et al. | |
| 4,349,921 A * | 9/1982 | Kuntz ........................ | 623/17.16 |
| 4,501,269 A | 2/1985 | Bagby | |
| 4,545,374 A | 10/1985 | Jacobson | |
| 4,646,738 A | 3/1987 | Trott | |
| 4,657,550 A | 4/1987 | Daher | |
| 4,743,256 A | 5/1988 | Brantigan | |
| 4,781,591 A | 11/1988 | Allen | |
| 4,834,757 A | 5/1989 | Brantigan | |
| 4,877,020 A | 10/1989 | Vich | |
| 4,878,915 A | 11/1989 | Brantigan | |
| 4,932,975 A | 6/1990 | Main et al. | |
| 4,950,296 A | 8/1990 | McIntyre | |

(Continued)

FOREIGN PATENT DOCUMENTS

CA    2015507    1/1999

(Continued)

OTHER PUBLICATIONS

Alleyne, Cargill, H., et al., "Current and future approaches to lumbar disc surgery: A literature review", *Medscape Orthopedics & Sports Medicine*, 1, [www.medscape.com/Medscape/OrthoSportsMed/1997/v01.n11/.../mos3057], (1997).

(Continued)

*Primary Examiner* — Eduardo C Robert
*Assistant Examiner* — Stuart S Bray
(74) *Attorney, Agent, or Firm* — Fish & Richardson P.C.

(57) ABSTRACT

A system and method for spinal fusion comprising a spinal fusion implant of non-bone construction releasably coupled to an insertion instrument dimensioned to introduce the spinal fusion implant into any of a variety of spinal target sites.

28 Claims, 20 Drawing Sheets

U.S. PATENT DOCUMENTS

| | | |
|---|---|---|
| 4,961,740 A | 10/1990 | Ray et al. |
| 4,962,766 A | 10/1990 | Herzon |
| 5,015,247 A | 5/1991 | Michelson |
| 5,026,373 A | 6/1991 | Ray et al. |
| 5,047,055 A | 9/1991 | Bao et al. |
| 5,055,104 A | 10/1991 | Ray |
| 5,062,845 A | 11/1991 | Kuslich et al. |
| 5,071,437 A | 12/1991 | Steffee |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharodi |
| 5,192,327 A | 3/1993 | Brantigan |
| 5,217,497 A | 6/1993 | Mehdian |
| 5,263,953 A | 11/1993 | Bagby |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,397,364 A | 3/1995 | Kozak |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,688 A | 7/1996 | Navas |
| 5,545,222 A | 8/1996 | Bonutti |
| 5,562,736 A | 10/1996 | Ray et al. |
| 5,565,005 A | 10/1996 | Erickson et al. |
| 5,571,190 A | 11/1996 | Ulrich |
| 5,571,192 A | 11/1996 | Schonhoffer |
| 5,593,409 A | 1/1997 | Michelson |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Marguiles |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,373 A | 1/1998 | Sevrain et al. |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,779,642 A | 7/1998 | Nightengale |
| 5,782,830 A | 7/1998 | Farris |
| 5,782,919 A | 7/1998 | Zdeblick et al. |
| 5,785,710 A | 7/1998 | Michelson |
| 5,797,909 A | 8/1998 | Michelson |
| 5,797,917 A * | 8/1998 | Boyd et al. ................. 606/99 |
| 5,800,549 A | 9/1998 | Bao et al. |
| 5,800,550 A | 9/1998 | Sertich |
| 5,814,084 A | 9/1998 | Grivas et al. |
| 5,851,208 A | 12/1998 | Trott |
| 5,860,973 A | 1/1999 | Michelson |
| 5,865,845 A | 2/1999 | Thalgott |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,890 A | 4/1999 | Pisharodi |
| 5,904,719 A | 5/1999 | Errico et al. |
| 5,910,315 A | 6/1999 | Stevenson et al. |
| 5,942,698 A | 8/1999 | Stevens |
| 5,954,769 A | 9/1999 | Rosenlicht |
| 5,968,098 A | 10/1999 | Winslow |
| 5,993,474 A | 11/1999 | Ouchi |
| 6,003,426 A | 12/1999 | Kobayashi et al. |
| 6,004,326 A | 12/1999 | Castro et al. |
| 6,008,433 A | 12/1999 | Stone |
| 6,015,436 A | 1/2000 | Schunhuffer |
| 6,033,405 A | 3/2000 | Winslow et al. |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,059,829 A | 5/2000 | Schlapfer et al. |
| 6,063,088 A | 5/2000 | Winslow |
| 6,083,225 A | 7/2000 | Winslow et al. |
| 6,096,080 A | 8/2000 | Nicholson et al. |
| 6,102,948 A | 8/2000 | Brosnahan, III |
| 6,120,503 A | 9/2000 | Michelson |
| 6,120,506 A | 9/2000 | Kohrs et al. |
| 6,132,472 A | 10/2000 | Bonutti |
| 6,143,033 A | 11/2000 | Paul et al. |
| 6,159,211 A | 12/2000 | Boriani et al. |
| 6,159,215 A | 12/2000 | Urbahns et al. |
| 6,193,756 B1 | 2/2001 | Studer et al. |
| 6,200,347 B1 | 3/2001 | Anderson |
| 6,224,607 B1 | 5/2001 | Michelson |
| 6,224,631 B1 | 5/2001 | Kohrs |
| 6,241,769 B1 | 6/2001 | Nicholson et al. |
| 6,241,771 B1 | 6/2001 | Gresser et al. |
| 6,251,140 B1 | 6/2001 | Marino et al. |
| 6,258,125 B1 | 7/2001 | Paul et al. |
| 6,277,149 B1 | 8/2001 | Boyle et al. |
| 6,319,257 B1 | 11/2001 | Carignan et al. |
| 6,371,989 B1 | 4/2002 | Chauvin et al. |
| 6,383,221 B1 | 5/2002 | Scarborough et al. |
| 6,409,766 B1 | 6/2002 | Brett |
| 6,425,772 B1 | 7/2002 | Bernier et al. |
| 6,432,140 B1 | 8/2002 | Lin |
| 6,440,142 B1 | 8/2002 | Ralph et al. |
| 6,442,814 B1 | 9/2002 | Landry et al. |
| 6,447,547 B1 | 9/2002 | Michelson |
| 6,454,806 B1 | 9/2002 | Cohen et al. |
| 6,468,311 B2 | 10/2002 | Boyd et al. |

| | | |
|---|---|---|
| 6,491,724 B1 | 12/2002 | Ferree |
| 6,527,773 B1 | 3/2003 | Lin et al. |
| 472,634 A1 | 4/2003 | Anderson |
| 473,650 A1 | 4/2003 | Anderson |
| 6,547,823 B2 | 4/2003 | Scarborough et al. |
| 6,595,998 B2 | 7/2003 | Johnson et al. |
| 6,626,905 B1 | 9/2003 | Schmiel et al. |
| 6,635,086 B2 | 10/2003 | Lin |
| 6,648,895 B2 | 11/2003 | Burkus et al. |
| 6,672,019 B1 | 1/2004 | Wenz |
| 6,676,703 B2 | 1/2004 | Biscup |
| 6,706,067 B2 | 3/2004 | Shimp et al. |
| 6,743,255 B2 | 6/2004 | Ferree |
| 6,746,484 B1 | 6/2004 | Liu et al. |
| 6,755,841 B2 | 6/2004 | Fraser et al. |
| 6,761,739 B2 | 7/2004 | Shepard |
| 6,824,564 B2 | 11/2004 | Crozet |
| 6,830,570 B1 * | 12/2004 | Frey et al. .................. 623/17.16 |
| 503,801 A1 | 4/2005 | Jackson |
| 6,923,814 B1 | 8/2005 | Hildebrand et al. |
| 6,942,698 B1 | 9/2005 | Jackson |
| 6,964,687 B1 | 11/2005 | Bernard et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,416 B2 | 3/2006 | Hanson et al. |
| 530,423 A1 | 10/2006 | Miles et al. |
| 2002/0058950 A1 | 5/2002 | Winterbottom et al. |
| 2002/0116008 A1 * | 8/2002 | Lin et al. ........................ 606/99 |
| 2003/0105528 A1 | 6/2003 | Shimp et al. |
| 2003/0139812 A1 | 7/2003 | Garcia et al. |
| 2004/0153155 A1 | 8/2004 | Chung et al. |
| 2005/0197702 A1 | 9/2005 | Coppes et al. |
| 2007/0191945 A1 | 8/2007 | Yu et al. |

FOREIGN PATENT DOCUMENTS

| | | |
|---|---|---|
| EP | 0369603 | 5/1990 |
| EP | 0517030 | 5/1992 |
| EP | 0667127 | 8/1995 |
| EP | 0706876 | 4/1996 |
| EP | 0716840 | 6/1996 |
| EP | 0737448 | 10/1996 |
| EP | 0796593 | 9/1997 |
| EP | 0880938 | 2/1998 |
| EP | 0809974 | 4/1998 |
| EP | 0809975 | 4/1998 |
| EP | 0811356 | 4/1998 |
| WO | WO 90/00037 | 1/1990 |
| WO | WO 91/06261 | 5/1992 |
| WO | WO 92/14423 | 9/1992 |
| WO | WO 94/04100 | 3/1994 |
| WO | WO 94/10928 | 5/1994 |
| WO | WO 95/01810 | 1/1995 |
| WO | WO 96/08205 | 3/1996 |
| WO | WO 96/17564 | 3/1996 |
| WO | WO 96/41582 | 12/1996 |
| WO | WO 97/20513 | 6/1997 |
| WO | WO 97/33525 | 9/1997 |
| WO | WO 97/37620 | 10/1997 |
| WO | WO 98/09586 | 3/1998 |
| WO | WO 98/14142 | 4/1998 |
| WO | WO 98/17208 | 4/1998 |
| WO | WO 98/25539 | 6/1998 |
| WO | WO 99/08627 | 2/1999 |
| WO | WO 99/38461 | 8/1999 |
| WO | WO 00/45712 | 8/2000 |
| WO | WO 00/45713 | 8/2000 |
| WO | WO 01/41681 | 6/2001 |
| WO | WO 01/49333 | 7/2001 |

OTHER PUBLICATIONS

Baulot, et al., "Complementary anterior spondylodesis by thoracoscopy. Technical note regarding an observation", *Lyon Surg.*, 90(5):347-351 (1994).

Benini, et al., "Undercutting decompression and posterior fusion with translaminar facet screw fixation in degenerative lumbar spinal stenosis: Technique and results", *Neuro-Orthopedics*, 17/18, 159-172 (1995).

Berry, et al., "A morphometric study of human lumbar and selected thoracic vertebrae, study of selected vertebrae" *Spine* 12(4):362-367 (1996).

Crock. H. V., "Anterior Lumbar Interbody Fusion" *Clinical Orthopaedics & Related Research*, Marshall R. Urist, Editor-in-Chief, J. B. Lippincott Company (1982).

Crock, H. V., "A Short Practice of Spinal Surgery", Second, revised edition, published by Springer-Verlag/Wein, New York (1993).

Edeland, H.G., "Some additional suggestions for an intervertebral disc prosthesis", *Journal of Biomedical Engineering*, 7:57-62 (1985).

Kambin, et al., "History and current status of percutaneous arthroscopic disc surgery", *Spine*, 21(24S):57S-61S (1996).

Kemp, H. B. S., "Anterior fusion of the spine for infective lesions in adults", *Journal of Bone & Joint Surgery*, 55B(4):715-734 (1973).

Nuvasive, Inc., Corrected Final Invalidity Contentions Regarding US 5,860,973, US 6,592,586 and US 6,945,933 filed in the United States District Court, Southern District of California on Jun. 14, 2010 (and 23 appendices).

Stein, et al., "Percutaneous facet joint fusion: Preliminary experience", *Journal of Vascular and Interventional Radiology*, 4:69-74 (1993).

Vamvanij, et al., "Surgical treatment of internal disc disruption: An outcome study of four fusion techniques", *Journal of Spinal Disorders*, 11(5):375-382 (1998).

CoRoent™ Marketing Brochure (9004001 A.0), *NuVasive, Inc.*, 2004, 2 pages.

CoRoent™ Marketing Brochure (9004001 C.0), *NuVasive, Inc.*, 2005, 2 pages.

CoRoent™ XL & XLR Marketing Brochure (9004225 A.0), *NuVasive, Inc.*, 2005, 2 pages.

CoRoent® XL & XLR Marketing Brochure (9004225 B.0), *NuVasive, Inc.*, 2006, 2 pages.

CoRoent® XL & XLR Marketing Brochure (9004225 C.0), *NuVasive, Inc.*, 2007, 2 pages.

CoRoent® XL Marketing Brochure (9500039 A.0), *NuVasive, Inc.*, 2006, 8 pages.

\* cited by examiner

SYSTEM AND METHODS FOR SPINAL FUSION

CROSS-REFERENCE TO RELATED APPLICATION

This application is continuation of U.S. patent application Ser. No. 11/093,409 filed Mar. 29, 2005 now U.S. Pat. No. 7,918,891, which claims the benefit of the filing date under 35 USC 119(e) of U.S. Provisional Application entitled "Systems and Methods for Spinal Fusion," Ser. No. 60/557,536 filed Mar. 29, 2004, the entire contents of which are incorporated herein by reference.

BACKGROUND OF THE INVENTION

I. Field of the Invention

The present invention relates generally to spinal surgery and, more particularly, to a system and method for spinal fusion comprising a spinal fusion implant of non-bone construction releasably coupled to an insertion instrument dimensioned to introduce the spinal fusion implant into any of a variety of spinal target sites.

II. Discussion of the Prior Art

Currently there are nearly 500,000 spine lumbar and cervical fusion procedures performed each year in the United States. Such procedures are commonly performed to correct problems, such as chronic back or neck pain, which result from degenerated intervertebral discs or trauma. Generally, spinal fusion procedures involve removing some or all of the diseased or damaged disc, and inserting one or more intervertebral implants into the resulting disc space. Introducing the intervertebral implant serves to restore the height between adjacent vertebrae ("disc height"), which reduces if not eliminates neural impingement commonly associated with a damaged or diseased disc.

Autologous bone grafts are widely used intervertebral implant for lumbar fusion. Autologous bone grafts are obtained by harvesting a section of bone from the iliac crest of the patient and thereafter implanting the article of autologous bone graft to effect fusion. While generally effective, the use of autologous bone grafts suffers certain drawbacks. A primary drawback is the morbidity associated with harvesting the autologous graft from the patient's iliac crest. Another related drawback is the added surgical time required to perform the bone-harvesting.

Allograft bone grafts have been employed with increased regularity in an effort to overcome the drawbacks of autologous bone grafts. Allograft bone grafts are harvested from cadaveric specimens, machined, and sterilized for implantation. While allograft bone grafts eliminate the morbidity associated with iliac crest bone harvesting, as well as decrease the overall surgical time, they still suffer certain drawbacks. A primary drawback is supply constraint, in that the tissue banks that process and produce allograft bone implants find it difficult to forecast allograft given the inherent challenges in forecasting the receipt of cadavers. Another related drawback is that it is difficult to manufacture the allograft with consistent shape and strength characteristics given the variation from cadaver to cadaver.

The present invention is directed at overcoming, or at least improving upon, the disadvantages of the prior art.

SUMMARY OF THE INVENTION

The present invention overcomes the drawbacks of the prior art by providing a spinal fusion system and related methods involving the use of a spinal fusion implant of non-bone construction. The non-bone construction of the spinal fusion implant of the present invention overcomes the drawbacks of the prior art in that it is not supply limited (as with allograft) and does not require harvesting bone from the patient (as with autograft). The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal or any combination of these materials.

The spinal fusion implant of the present invention may be provided in any number of suitable shapes and sizes depending upon the particular surgical procedure or need. The spinal fusion implant of the present invention may be dimensioned for use in the cervical and/or lumbar spine without departing from the scope of the present invention. For lumbar fusion, the spinal fusion implant of the present invention may be dimensioned, by way of example only, having a width ranging between 9 and 18 mm, a height ranging between 8 and 16 mm, and a length ranging between 25 and 45 mm. For cervical fusion, the spinal fusion implant of the present invention may be dimensioned, by way of example only, having a width about 11 mm, a height ranging between 5 and 12 mm, and a length about 14 mm.

The spinal fusion implant of the present invention may be provided with any number of additional features for promoting fusion, such as apertures extending between the upper and lower vertebral bodies which allow a boney bridge to form through the spinal fusion implant of the present invention. Such fusion-promoting apertures may be dimensioned to receive any number of suitable osteoinductive agents, including but not limited to bone morphogenic protein (BMP) and bio-resorbable polymers, including but not limited to any of a variety of poly (D,L-lactide-co-glycolide) based polymers. The spinal fusion implant of the present invention is preferably equipped with one or more lateral openings which aid it provides in visualization at the time of implantation and at subsequent clinical evaluations.

The spinal fusion implant of the present invention may be provided with any number of suitable anti-migration features to prevent spinal fusion implant from migrating or moving from the disc space after implantation. Suitable anti-migration features may include, but are not necessarily limited to, angled teeth formed along the upper and/or lower surfaces of the spinal fusion implant and/or spike elements disposed partially within and partially outside the upper and/or lower surfaces of the spinal fusion implant. Such anti-migration features provide the additional benefit of increasing the overall surface area between the spinal fusion implant of the present invention and the adjacent vertebrae, which promotes overall bone fusion rates.

The spinal fusion implant of the present invention may be provided with any number of features for enhancing the visualization of the implant during and/or after implantation into a spinal target site. According to one aspect of the present invention, such visualization enhancement features may take the form of the spike elements used for anti-migration, which may be manufactured from any of a variety of suitable materials, including but not limited to a metal, ceramic, and/or polymer material, preferably having radiopaque characteristics. The spike elements may also take any of a variety of suitable shapes, including but not limited to a generally elongated element disposed within the implant such that the ends thereof extend generally perpendicularly from the upper and/or lower surfaces of the implant. The spike elements may each comprise a unitary element extending through upper and lower surfaces or, alternatively, each spike element may comprise a shorter element which only extends through a single surface (that is, does not extend through the entire height of the implant). In any event, when the spike elements are provided having radiodense characteristics and the implant is manufactured from a radiolucent material (such as, by way of example only, PEEK and/or PEKK), the spike elements will be readily observable under X-ray or fluoroscopy such that a surgeon may track the progress of the implant during implantation and/or the placement of the implant after implantation.

The spinal implant of the present invention may be introduced into a spinal target site through the use of any of a variety of suitable instruments having the capability to releasably engage the spinal implant. In a preferred embodiment, The insertion instrument permits quick, direct, accurate placement of the spinal implant of the present invention into the intervertebral space. According to one embodiment, the insertion instrument includes a threaded engagement element dimensioned to threadably engage into a receiving aperture formed in the spinal fusion implant of the present invention. According to another embodiment, the insertion instrument includes an elongate fork member and a generally tubular lock member.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system to facilitate bone fusion and related methods disclosed herein boasts a variety of inventive features and components that warrant patent protection, both individually and in combination.

Figure 1:
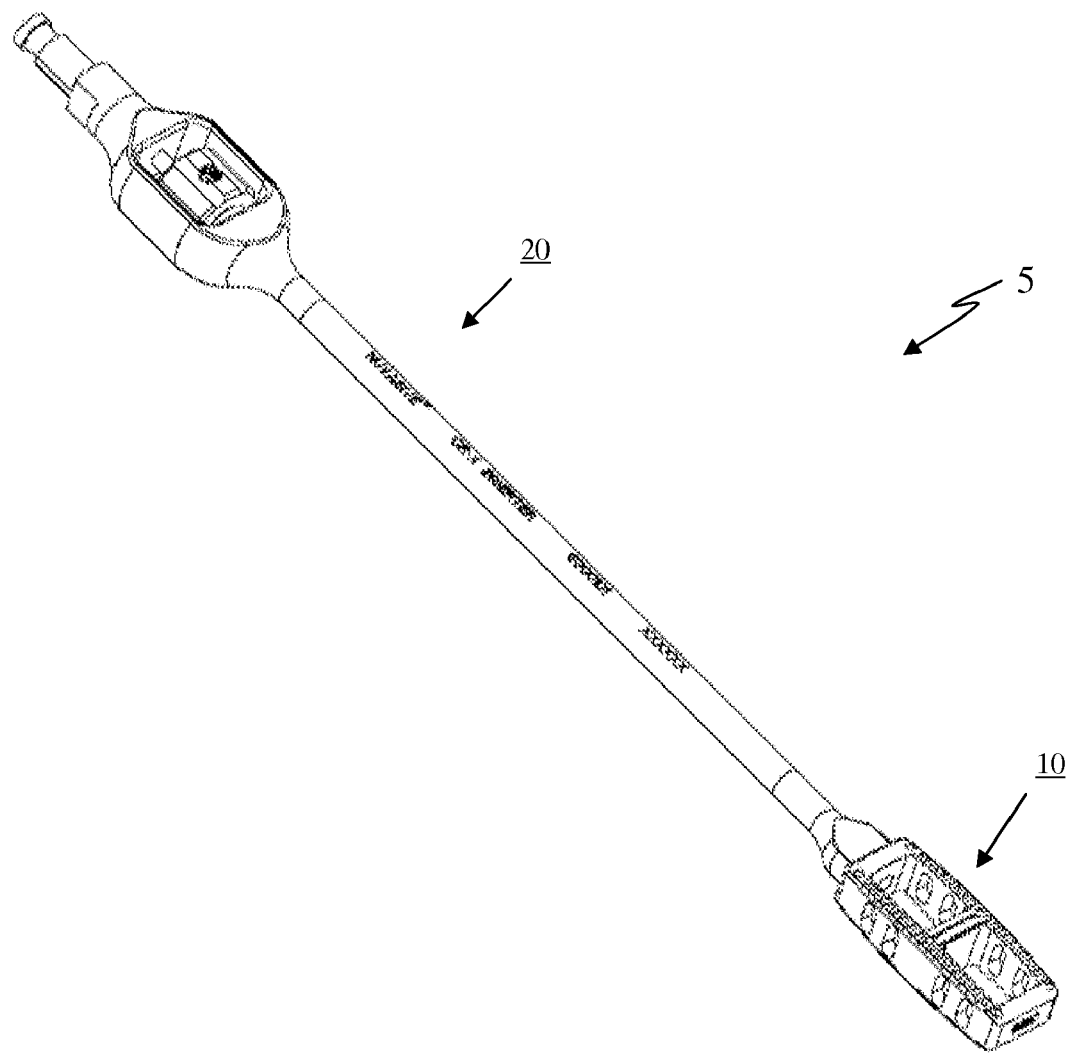
FIG. 1 is a perspective view of a spinal fusion system of the present invention, including a lumbar fusion implant releasably coupled to an insertion instrument according to one embodiment of the present invention.
Figure 2:
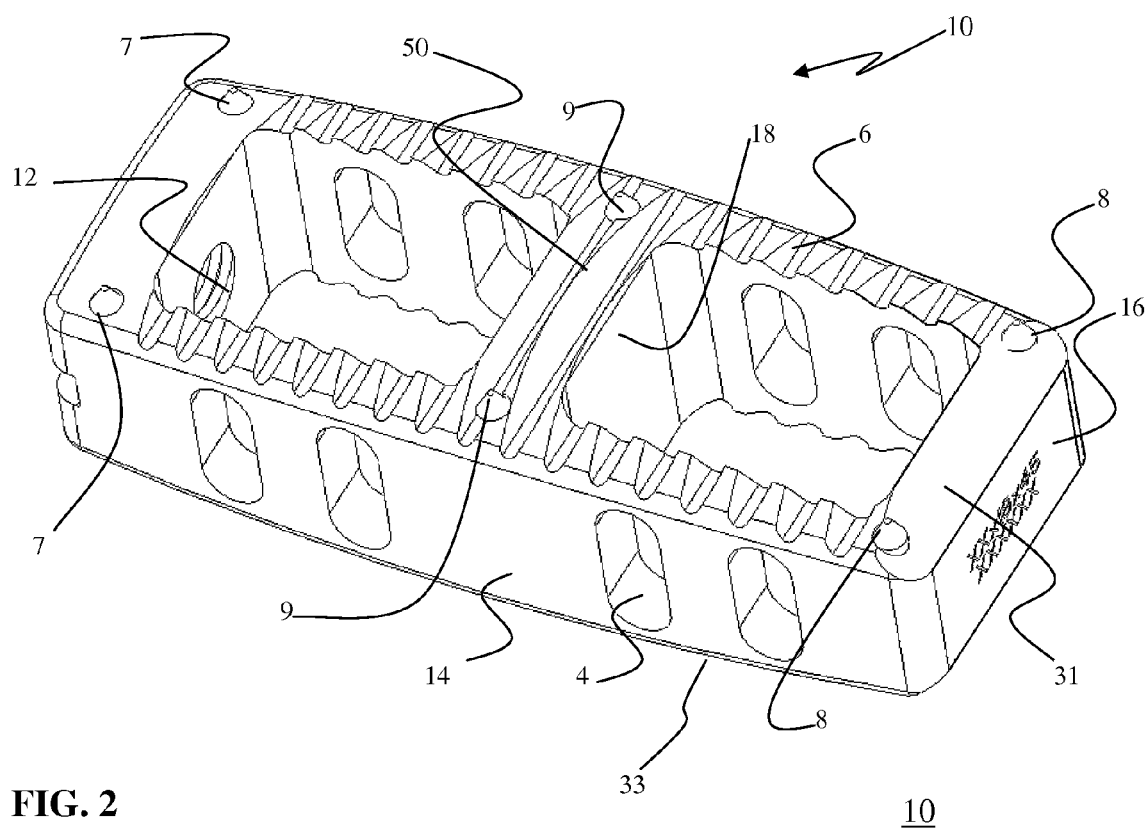
FIG. 2 is a perspective view of the lumbar fusion implant of FIG. 1, illustrating (among other things) fusion apertures extending between top and bottom surfaces, a plurality of visualization apertures extending through the side walls, and a variety of anti-migration features according to one embodiment of the present invention.
Figure 3:
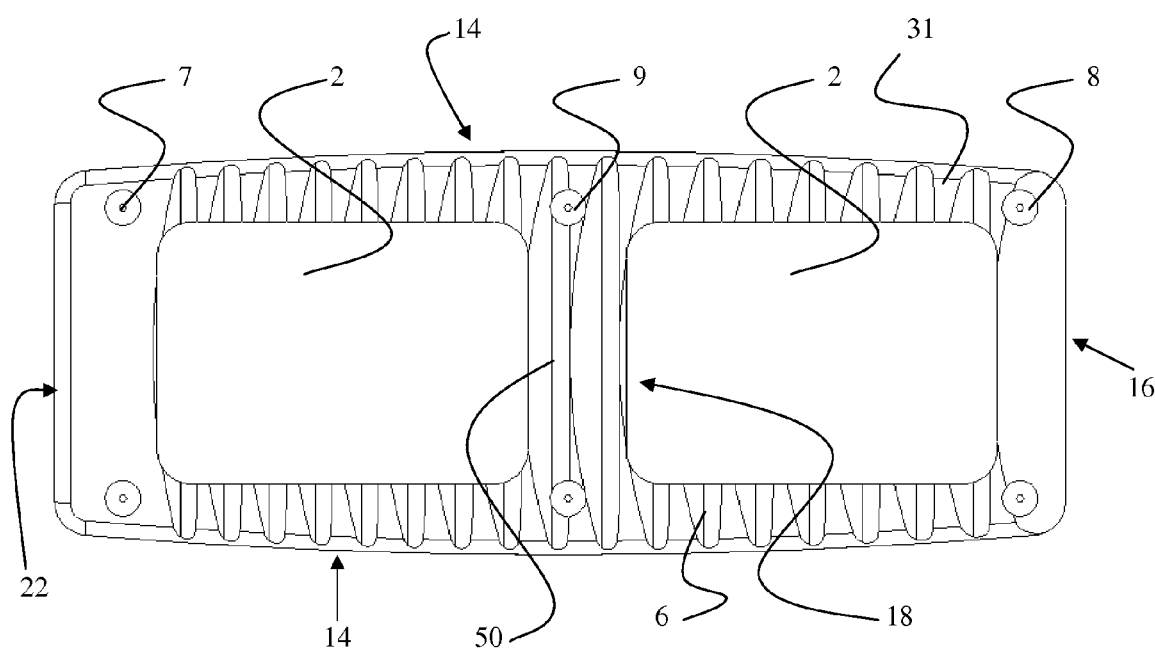
FIG. 3 is a top view of the lumbar fusion implant of FIG. 1, illustrating (among other things) the fusion apertures and the anti-migration features according to one embodiment of the present invention.
Figure 4:
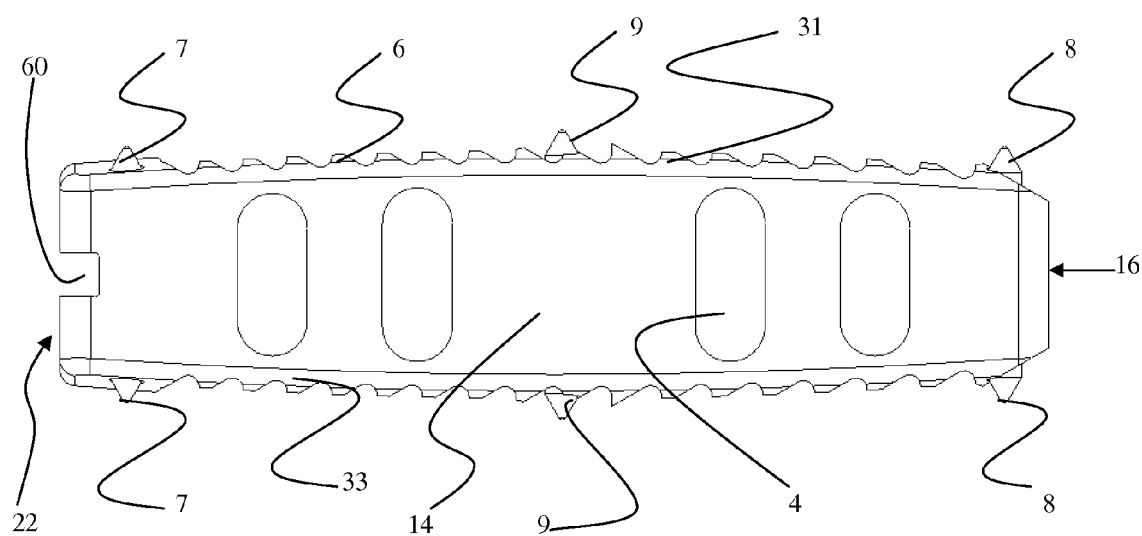
FIG. 4 is a side view of the lumbar fusion implant of FIG. 1, illustrating (among other things) the visualization apertures, the anti-migration feature, and a receiving aperture for releasably engaging the insertion instrument of FIG. 1 according to one embodiment of the present invention.
Figure 5:
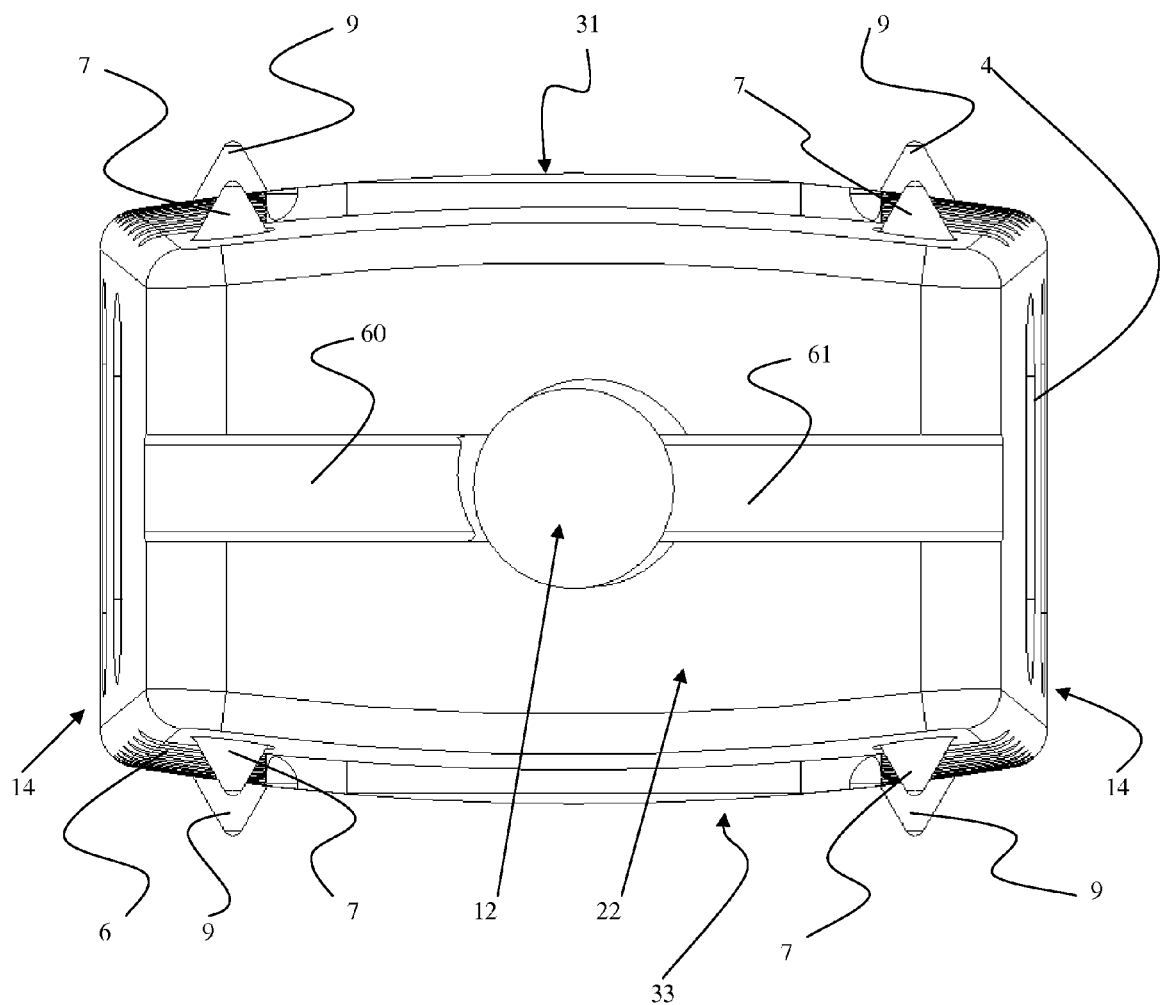
FIG. 5 is an end view of the lumbar fusion implant of FIG. 1, illustrating (among other things) the receiving aperture formed in the proximal end, the anti-migration features, and the visualization apertures according to one embodiment of the present invention.

FIG. 1 illustrates, by way of example only, a spinal fusion system 5 for performing spinal fusion between adjacent lumbar vertebrae, including an exemplary spinal fusion implant 10 and an exemplary insertion instrument 20 provided in accordance with the present invention. The spinal fusion implant 10 may be comprised of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. The spinal fusion implant 10 of the present invention may be dimensioned, by way of example only, having a width ranging between 9 and 18 mm, a height ranging between 8 and 16 mm, and a length ranging between 25 and 45 mm.

As will be described in detail below, the insertion instrument 20 is configured to releasably maintain the exemplary spinal fusion implant 10 in the proper orientation during insertion into a lumbar disc space and thereafter release to deposit the implant 10. The exemplary spinal fusion implant 10, having been deposited in the disc space, facilitates spinal fusion over time by maintaining a restored disc height as natural bone growth occurs through and/or past the implant 10, resulting in the formation of a boney bridge extending between the adjacent vertebral bodies. The implant 10 is particularly suited for introduction into the disc space via a lateral (trans-psoas) approach to the spine, but may be introduced in any of a variety of approaches, such as posterior, anterior, antero-lateral, and postero-lateral, without departing from the scope of the present invention (depending upon the sizing of the implant 10).

The spinal fusion implant 10 of the present invention may be provided with any number of additional features for promoting fusion, such as apertures 2 extending between the upper and lower vertebral bodies which allow a boney bridge to form through the spinal fusion implant 10. According to a still further aspect of the present invention, this fusion may be facilitated or augmented by introducing or positioning various osteoinductive materials within the apertures 2 and/or adjacent to the spinal fusion implant 10. Such osteoinductive materials may be introduced before, during, or after the insertion of the exemplary spinal fusion implant 10, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers.

The spinal fusion implant 10 of the present invention is preferably equipped with one or more visualization apertures 4 situated along the lateral sides, which aid in visualization at the time of implantation and at subsequent clinical evaluations. More specifically, based on the generally radiolucent nature of the implant 10, the visualization apertures 4 provide the ability to visualize the interior of the implant 10 during X-ray and/or other suitable imaging techniques which are undertaken from the side (or "lateral") perspective of the implant 10. If fusion has taken place, the visualization apertures 4 will provide a method for the surgeon to make follow up assessments as to the degree of fusion without any visual interference from the spinal fusion implant 10. Further, the visualization apertures 4 will provide an avenue for cellular migration to the exterior of the spinal fusion implant 10. Thus the spinal fusion implant 10 will serve as additional scaffolding for bone fusion on the exterior of the spinal fusion implant 10.

FIGS. 2-5 depict various embodiments of the exemplary spinal fusion implant 10. Some common attributes are shared among the various embodiments. More specifically, each spinal fusion implant 10 has a top surface 31, a bottom surface 33, lateral sides 14, a proximal side 22, and a distal side 16. In one embodiment, the top and bottom surfaces 31, 33 are generally parallel. It can be appreciated by one skilled in the art that although the surfaces 31, 33 are generally parallel to one another, they may be provided in any number of suitable shapes, including but not limited to concave and/or convex. When provided as convex shapes, the top and bottom surfaces 31, 33 may better match the natural contours of the vertebral end plates. Although not shown, it will be appreciated that the top and bottom surfaces 31, 33 may be angled relative to one another to better match the natural lordosis of the lumbar and cervical spine or the natural kyphosis of the thoracic spine The exemplary spinal fusion implant 10 also preferably includes anti-migration features designed to increase the friction between the spinal fusion implant 10 and the adjacent contacting surfaces of the vertebral bodies so as to prohibit migration of the spinal fusion implant 10 after implantation. Such anti-migration features may include ridges 6 provided along the top surface 31 and/or bottom surface 33. Additional anti-migration features may also include a pair of spike elements 7 disposed within the proximal region of the implant 10, a pair of spike elements 8 disposed within the distal region of the implant 10, and a pair of spike elements 9 disposed within the central region of the implant 10. Spike elements 7, 8, 9 may extend from the top surface 31 and/or bottom surface 33 within the respective proximal, distal and central regions of the implant 10. The spike elements 7, 8, 9 may be manufactured from any of a variety of suitable materials, including but not limited to a metal, ceramic, and/or polymer material, preferably having radiopaque characteristics. The spike elements 7, 8, 9 may also take any of a variety of suitable shapes, including but not limited to a generally elongated element disposed within the implant 10 such that the ends thereof extend generally perpendicularly from the upper and/or lower surfaces 31, 33 of the implant 10. As best appreciated in FIG. 4, the spike elements 7, 8, 9 may each comprise a unitary element extending through upper and lower surfaces 31, 33. Alternatively, each spike element 7, 8, 9 may comprise a shorter element which only extends through a single surface 31, 33 (that is, does not extend through the entire height of the implant 10). In any event, when the spike elements 7, 8, 9 are provided having radiodense characteristics and the implant 10 is manufactured from a radiolucent material (such as, by way of example only, PEEK and/or PEKK), the spike elements 7, 8, 9 will be readily observable under X-ray or fluoroscopy such that a surgeon may track the progress of the implant 10 during implantation and/or the placement of the implant 10 after implantation.

The spinal fusion implant 10 has two large fusion apertures 2, separated by a medial support 50, extending in a vertical fashion through the top surface 31 and bottom surface 33. The fusion apertures 2 function primarily as an avenue for bony fusion between adjacent vertebrae. The fusion apertures 2 may be provided in any of a variety of suitable shapes, including but not limited to the generally rectangular shape best viewed in FIG. 3, or a generally circular, oblong and/or triangular shape or any combination thereof. The spinal fusion implant 10 may have a plurality of visualization apertures 4 which allow a clinician to make visual observations of the degree of bony fusion un-obscured by the lateral side 14 to facilitate further diagnosis and treatment. The visualization apertures 4 may be provided in any of a variety of suitable shapes, including but not limited to the generally oblong shape best viewed in FIG. 4, or a generally circular, rectangular and/or triangular shape or any combination thereof.

The spinal fusion implant 10 may be provided with any number of suitable features for engaging the insertion instrument 20 without departing from the scope of the present invention. As best viewed in FIGS. 4-6, one engagement mechanism involves providing a threaded receiving aperture 12 in the proximal sidewall 22 of the spinal fusion implant 10 of the present invention. The threaded receiving aperture 12 is dimensioned to threadably receive a threaded connector 24 on the insertion instrument 20 (as will be described in greater detail below). The receiving aperture 12 extends inwardly from the proximal side 22 in a generally perpendicular fashion relative to the proximal side 22. Although shown as having a generally circular cross-section, it will be appreciated that the receiving aperture 12 may be provided having any number of suitable shapes or cross-sections, including but not limited to rectangular or triangular. In addition to the receiving aperture 12, the spinal fusion implant 10 is preferably equipped with a pair of grooved purchase regions 60, 61 extending generally horizontally from either side of the receiving aperture 12. The grooved purchase regions 60, 61 are dimensioned to receive corresponding distal head slots 62, 63 on the insertion instrument 20 (as will be described in greater detail below), which collectively provide an enhanced engagement between the implant 10 and instrument 20.

FIGS. 6-9 detail the exemplary insertion instrument 20 according to one embodiment of the invention. The exemplary insertion instrument 20 includes an elongate tubular element 28 and an inserter shaft 44. The elongate tubular element 28 is constructed with a distal head 26 at its distal end, distal head ridges 62, 63 on the distal end of the distal head 26, a thumbwheel housing 38 at its proximal end and a handle 42 at its proximal end. The elongate tubular element 28 is generally cylindrical and of a length sufficient to allow the device to span from the surgical target site to a location sufficiently outside the patient's body so the handle 42 and thumbwheel housing 38 can be easily accessed by a clinician or a complimentary controlling device.

The elongate tubular element 28 is dimensioned to receive a spring 46 and the proximal end of the inserter shaft 44 into the inner bore 64 of the elongate tubular element 28. The inserter shaft 44 is dimensioned such that the threaded connector 24 at the distal end of the inserter shaft 44 just protrudes past the distal head slots 62, 63 to allow engagement with the receiving aperture 12 of the spinal fusion implant 10. It should be appreciated by one skilled in the art that such a construction allows the inserter shaft 44 to be able to rotate freely within the elongate tubular element 28 while stabilized by a spring 46 to reduce any slidable play in the insertion instrument 20.

The handle 42 is generally disposed at the proximal end of the insertion instrument 20. The handle 42 is fixed to the thumbwheel housing 38 allowing easy handling by the clinician. Because the handle 42 is fixed the clinician has easy access to the thumbwheel 34 and can stably turn the thumbwheel 34 relative to the thumbwheel housing 38. Additionally, the relative orientation of the thumbwheel housing 38 to the handle 42 orients the clinician with respect to the distal head 26 and distal head slot 62. By way of example, the thumbwheel housing 38 holds a thumbwheel 34, a set screw 32, and a spacer 36. The inserter shaft 44 is attached to the thumbwheel 34 and is freely rotatable with low friction due to the spacer 36. One skilled in the art can appreciate myriad methods of assembling a housing similar to the above described.

Figure 6:
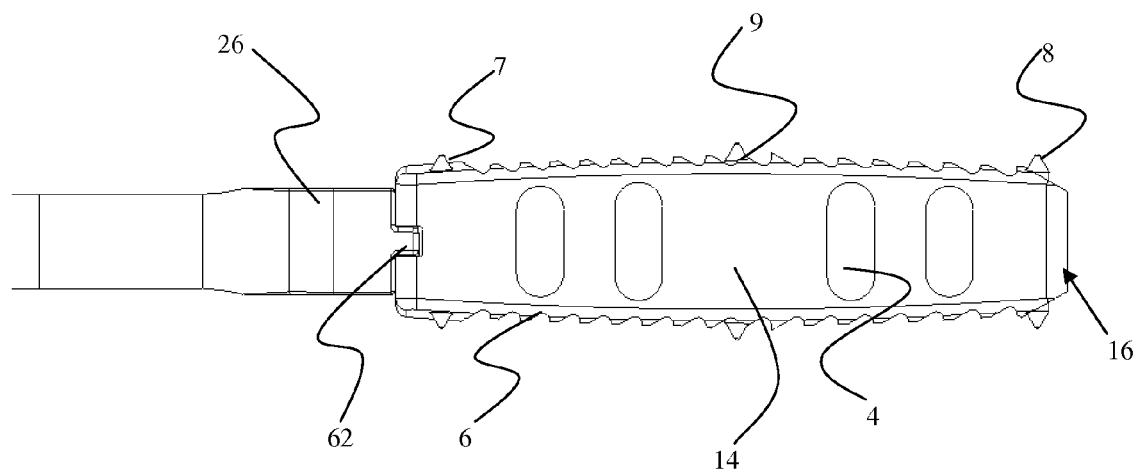
FIG. 6 is an enlarged side view of the lumbar fusion implant of FIG. 1 releasably coupled to the distal end of the insertion instrument of FIG. 1 according to one embodiment of the present invention.
Figure 7:
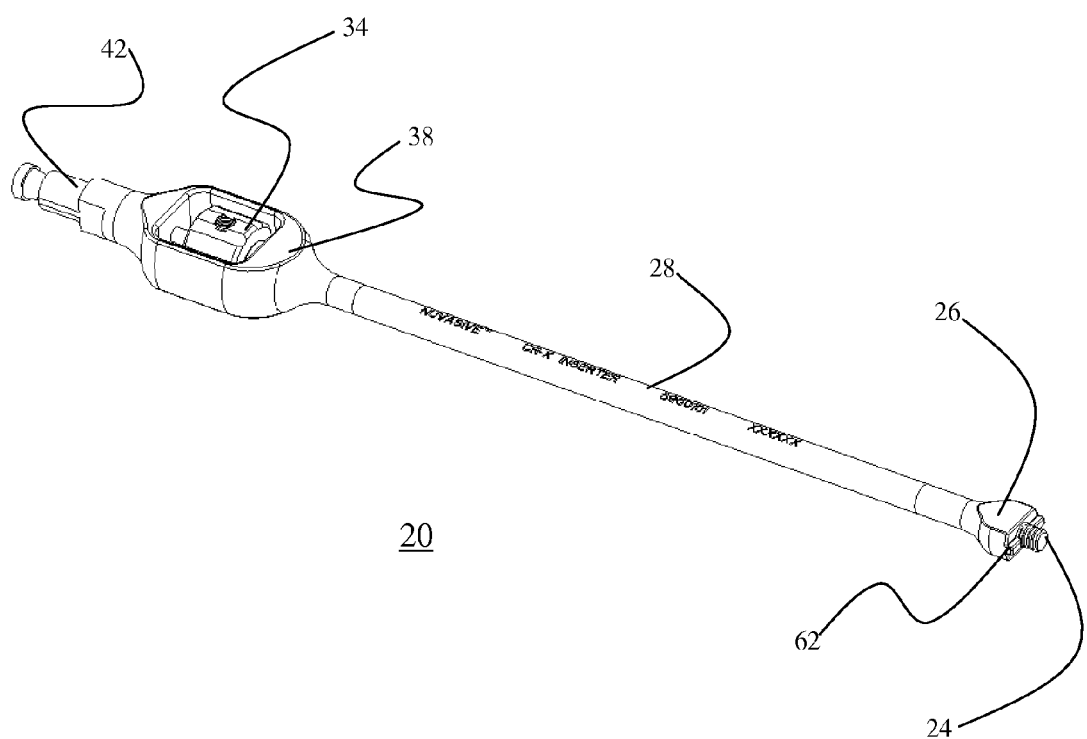
FIG. 7 is a perspective view of the insertion instrument of FIG. 1 in a fully assembled form according to one embodiment of the present invention.
Figure 8:
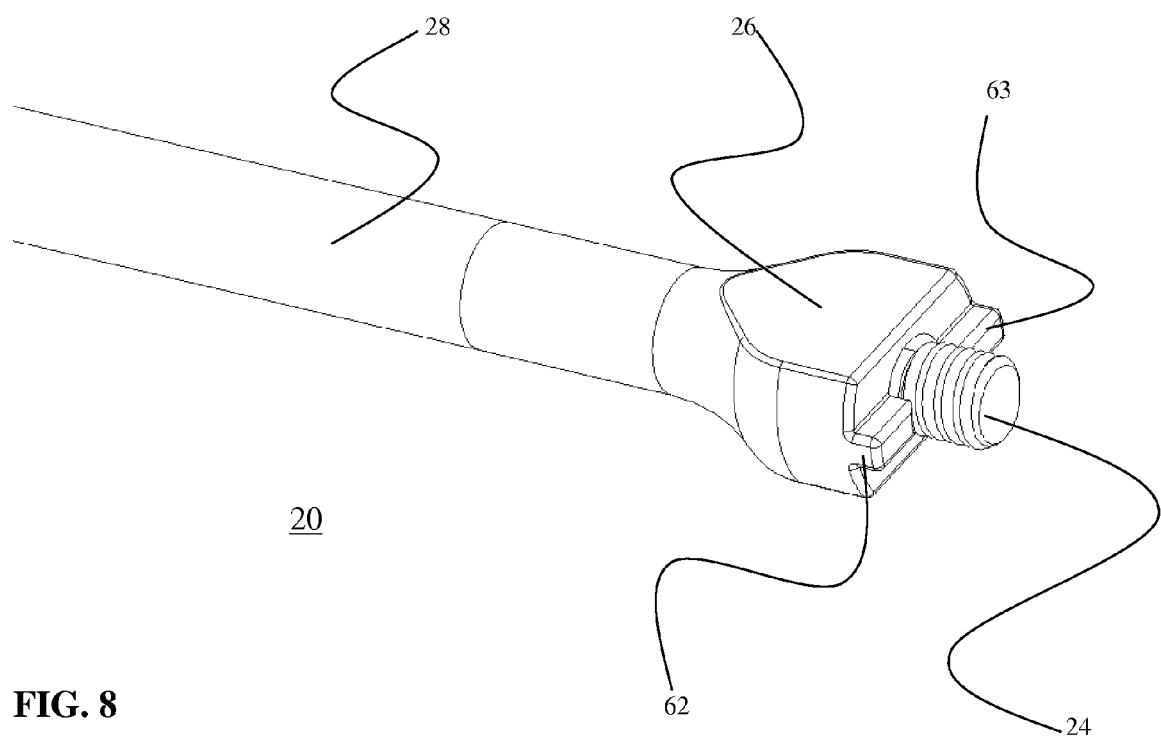
FIG. 8 is an enlarged perspective view of the distal region of the insertion instrument of FIG. 1 according to one embodiment of the present invention.
Figure 9:
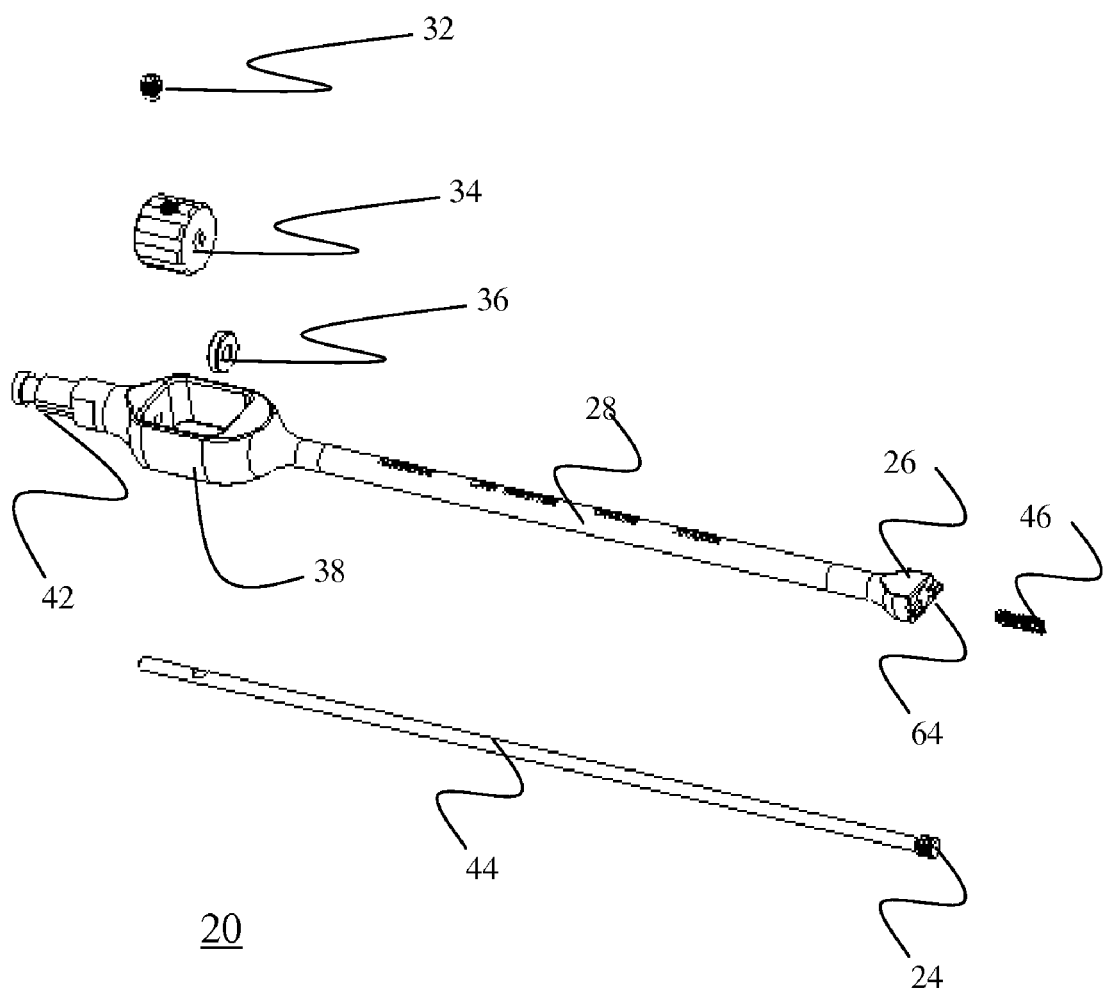
FIG. 9 is a perspective exploded view of the insertion instrument of FIG. 1, illustrating the component parts of the insertion instrument according to one embodiment of the present invention.

FIG. 6 details the distal head ridge of the exemplary insertion instrument 20 coupled to the spinal fusion implant 10 through the purchase regions 60, 61. The distal head slots 62, 63 are dimensioned to fit slidably into the purchase regions 60, 61 with low friction to allow accurate engagement of the threaded connector 24 to the receiving aperture 12 of the spinal fusion implant 10. In the presented embodiment, the outer dimension of the threaded connector 24 is smaller than the largest outer dimension of the distal head 26 and elongate tubular element 28. Alternatively, other methods of creating a gripping surface are contemplated including but not limited to knurling or facets.

In order to use the system to perform a spinal fusion procedure, the clinician must first designate the appropriate implant size. After the spinal fusion implant 10 is chosen, the distal head slots 62, 63 of the inserter shaft 44 are inserted into the purchase regions 60, 61 of the spinal fusion implant 10. At that time the spinal fusion implant 10 and insertion instrument 20 are slidably engaged with one another. Before the clinician can manipulate the combined spinal fusion implant 10 and insertion instrument 20, they must be releasably secured together. In order to secure the spinal fusion implant 10 onto the threaded connector 24 of the inserter instrument 20, the clinician employs the thumbwheel 34 to rotate the inserter shaft 44 and threaded connector 24. The rotation of the threaded connector 24 will releasably engage the receiving aperture of the spinal fusion implant 10 and stabilize the insertion instrument 20 relative to the spinal fusion implant 10.

A clinician can utilize the secured system in either an open or minimally invasive spinal fusion procedure. In either type of procedure, a working channel is created in a patient that reaches the targeted spinal level. After the creation of that channel, the intervertebral space may be prepared via any number of well known preparation tools, including but not limited to kerrisons, rongeurs, pituitaries, and rasps. After preparation, the insertion instrument 20 is used to place a spinal fusion implant 10 into the prepared intervertebral space. Once the implant 10 is inserted into the prepared space, the implant 10 is released from the insertion instrument 20 by rotating the thumbwheel 34 to disengage the threaded connector 24 from the receiving aperture 12. That motion removes the compressive force on the purchase regions 60, 61 between the distal head 26 and the distal head ridges 62, 63 of the spinal fusion implant 10 and allows the insertion instrument to be slidably removed from the implant 10. After the threaded connector 24 is disengaged from the implant 10, the insertion instrument 20 is removed from the working channel and the channel is closed. As previously mentioned, additional materials may be included in the procedure before, during or after the insertion of the spinal fusion implant 10 to aid the natural fusion of the targeted spinal level.

Figure 10:
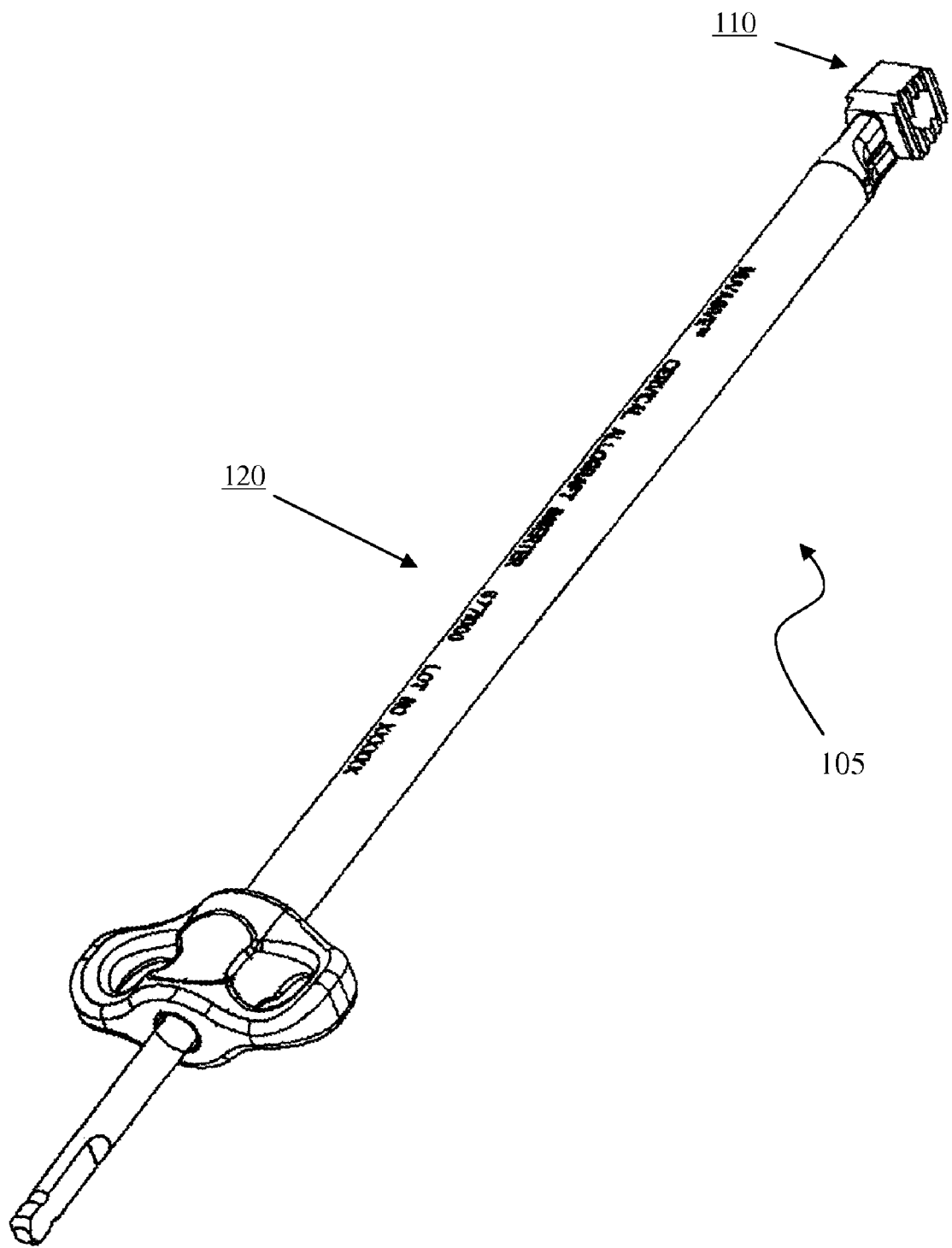
FIG. 10 is a perspective view of a spinal fusion system of the present invention, including a cervical fusion implant releasably coupled to a cervical insertion instrument according to one embodiment of the present invention.
Figure 11:
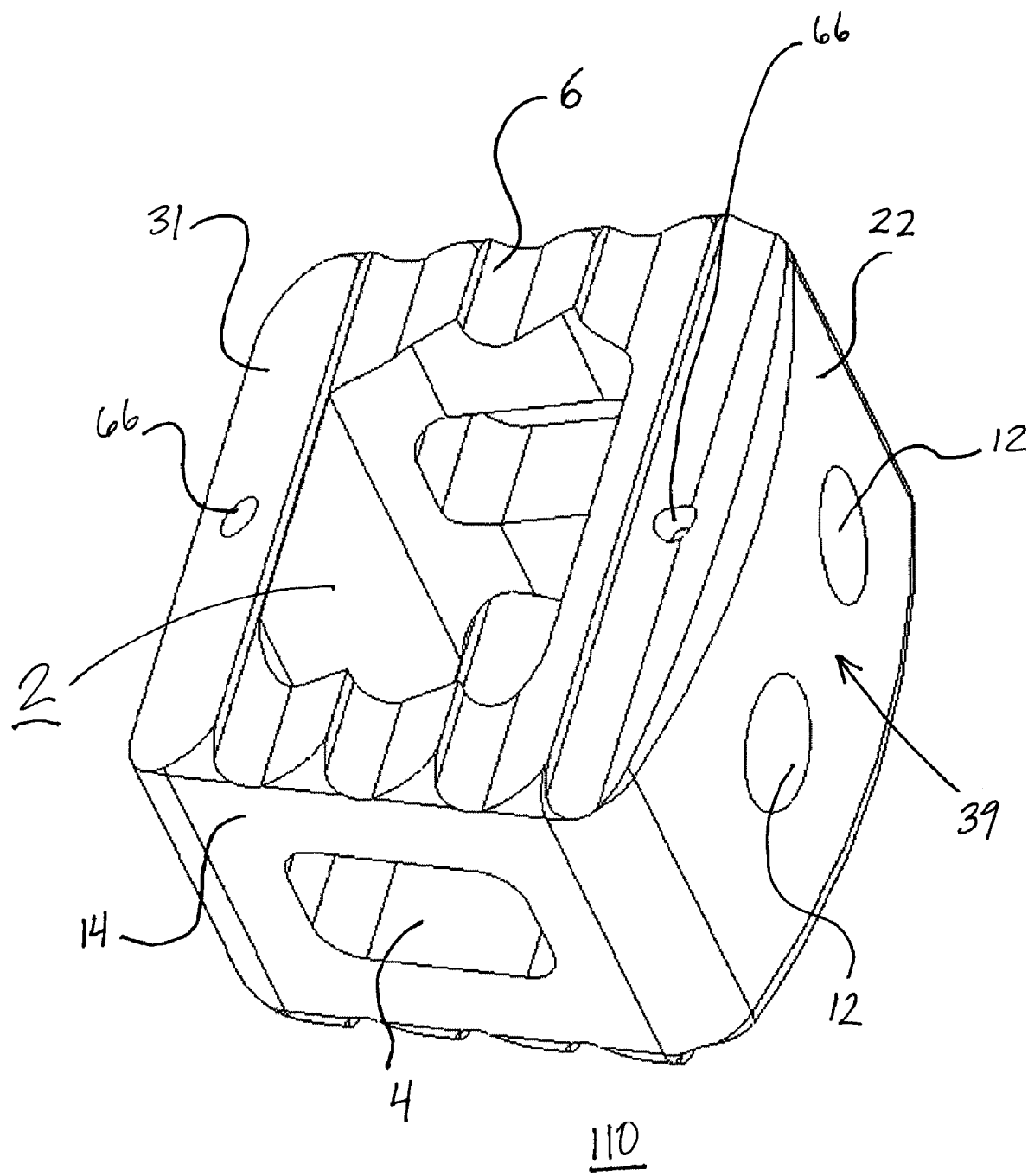
FIG. 11 is a perspective view of the proximal side of the cervical fusion implant of FIG. 10, illustrating (among other things) fusion apertures extending between top and bottom surfaces, a plurality of visualization apertures extending through the lateral walls, a plurality of receiving apertures, and a variety of anti-migration features according to one embodiment of the present invention.
Figure 12:
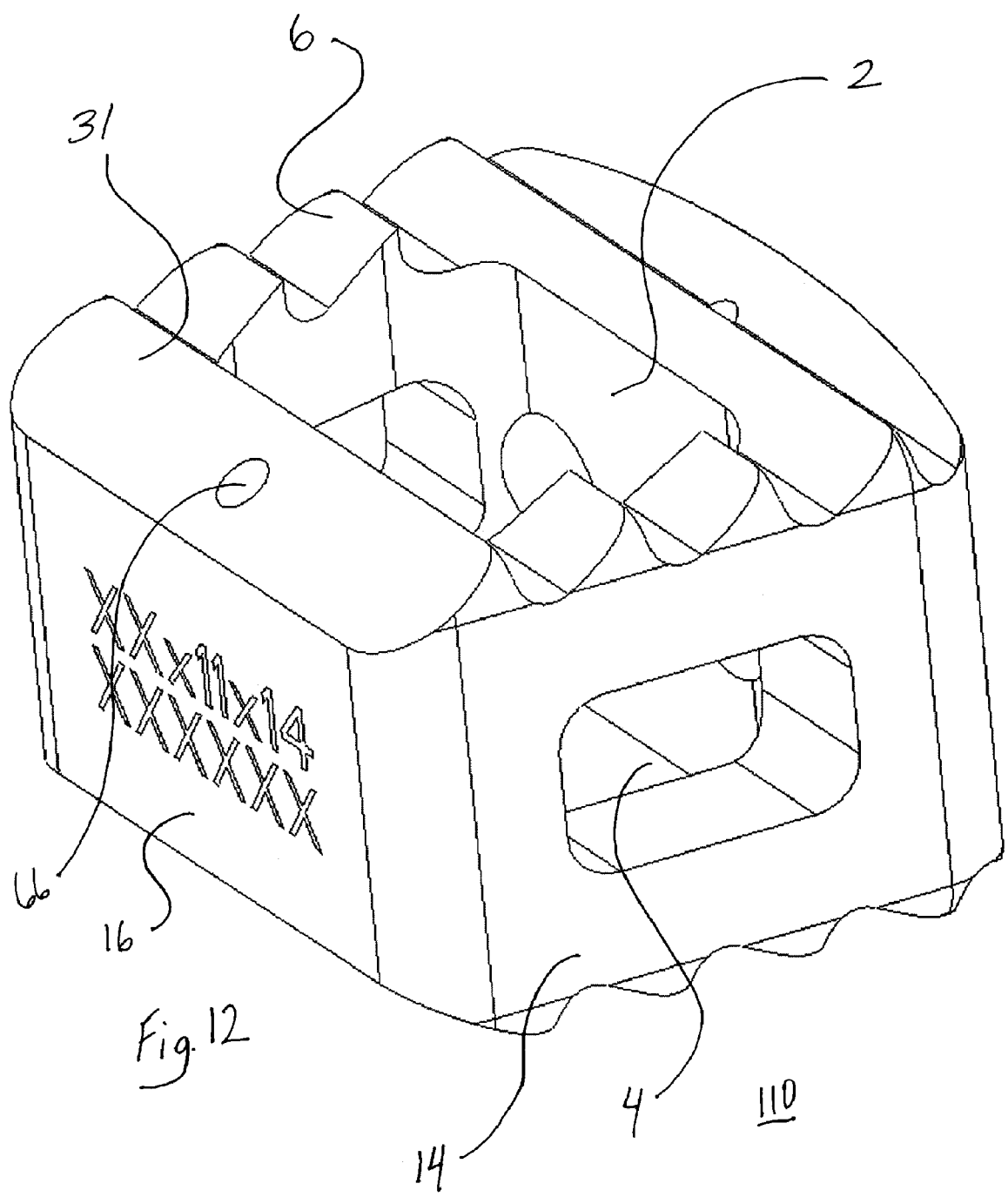
FIG. 12 is a perspective view of the distal side cervical fusion implant of FIG. 10, illustrating (among other things) the visualization apertures and anti-migration features.
Figure 13:
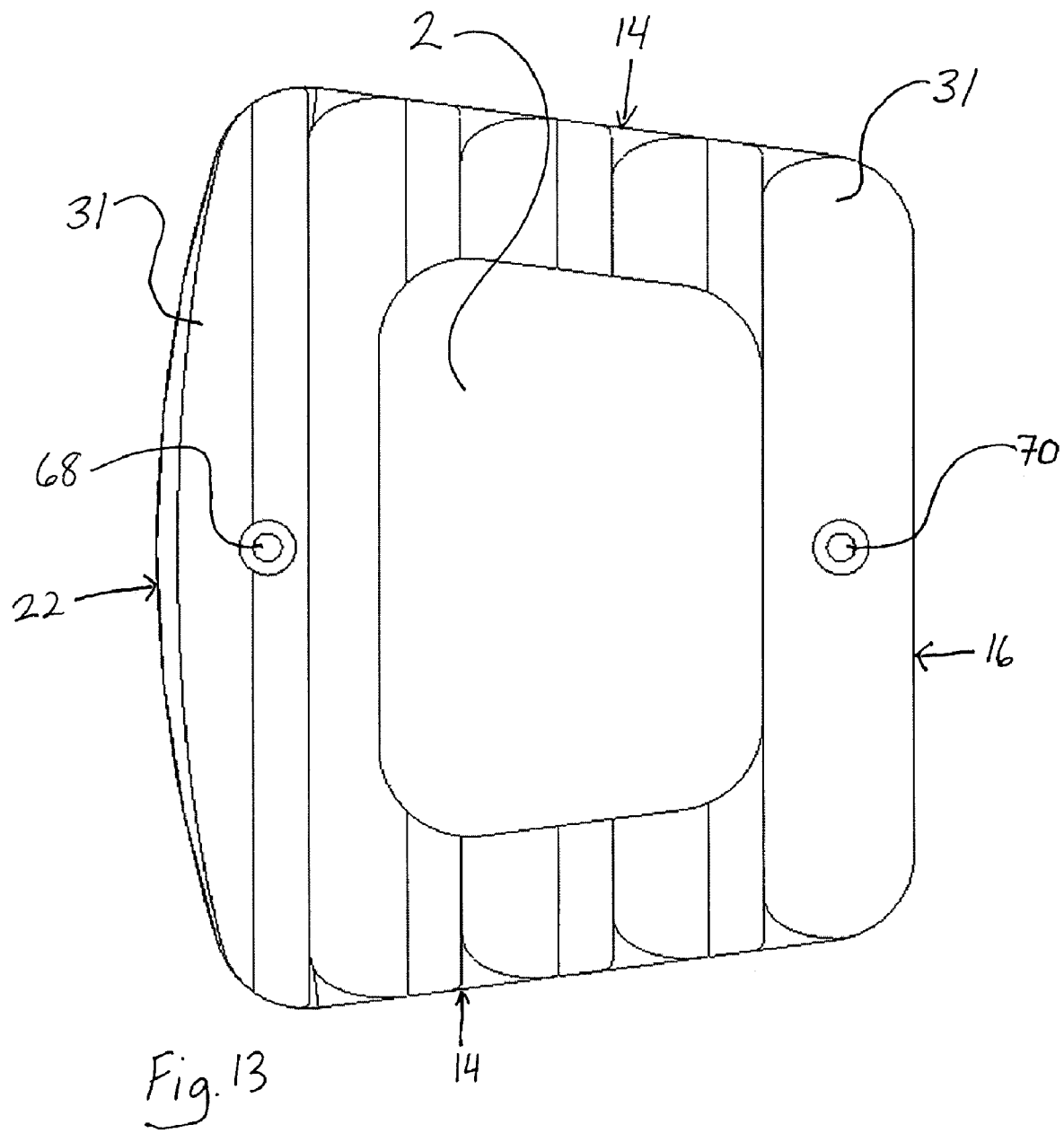
FIG. 13 is a top view of the cervical fusion implant of FIG. 10, illustrating (among other things) the fusion apertures and anti-migration features according to one embodiment of the present invention.
Figure 14:
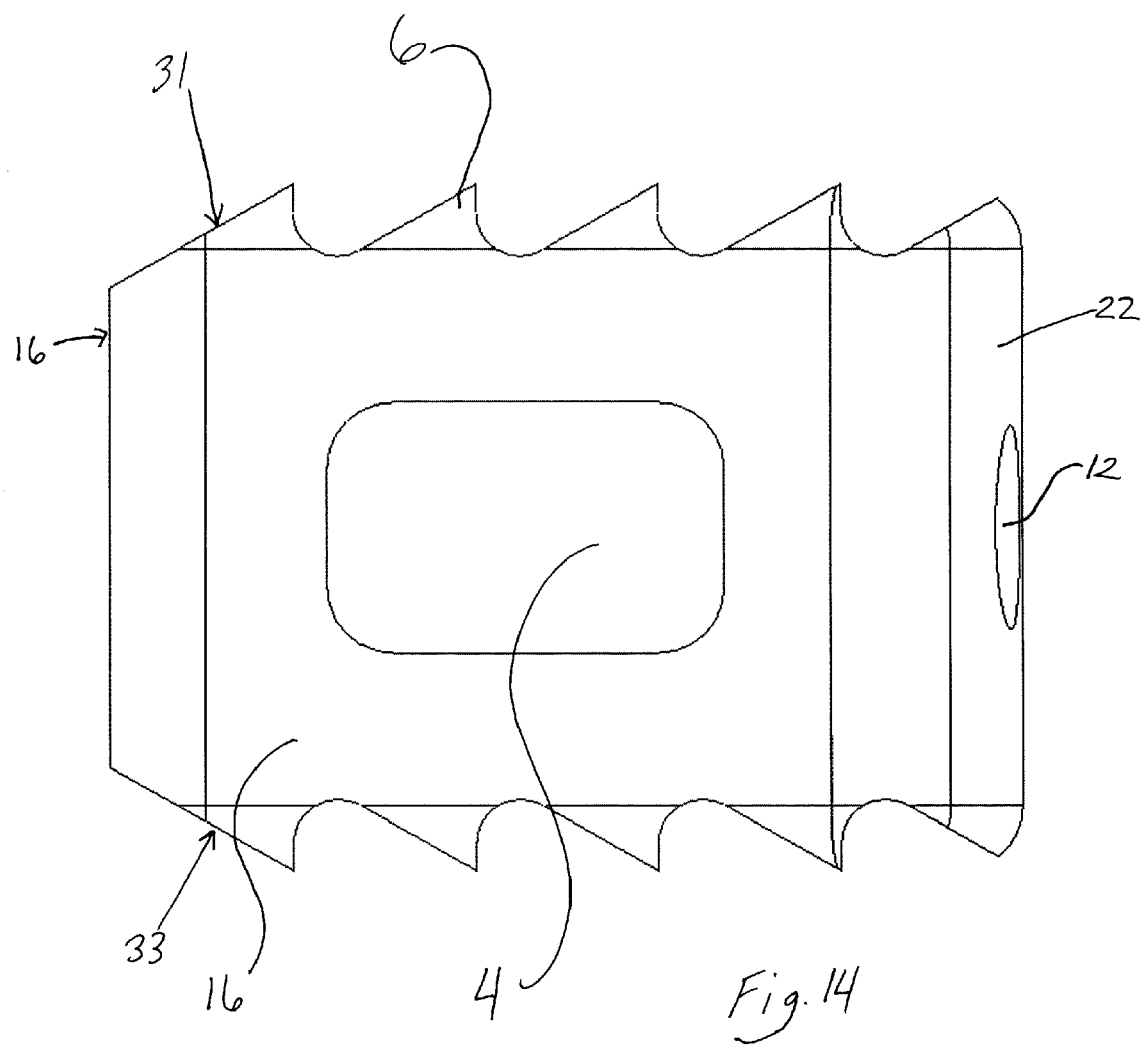
FIG. 14 is a side view of the cervical fusion implant of FIG. 10, illustrating (among other things) the visualization apertures, the anti-migration features, and one of two receiving apertures provided in the proximal end for releasably engaging the cervical insertion instrument of FIG. 10 according to one embodiment of the present invention.

FIG. 10 illustrates a spinal fusion system 105 for performing spinal fusion between adjacent cervical vertebrae, including an exemplary spinal fusion implant 110 and an exemplary cervical insertion instrument 120 provided in accordance with the present invention. The spinal fusion implant 110 may comprise of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. The spinal fusion implant 110 may be provided in any number of suitable sizes, such as, by way of example only, a length ranging between 11 to 14 mm, a height ranging between 5 and 12 mm, and a width ranging from 14 and 16 mm.

As will be described in detail below, the cervical insertion instrument 120 is configured to releasably maintain the exemplary cervical fusion implant 110 in the proper orientation for insertion. The cervical fusion implant 110 may be simultaneously introduced into a disc space while locked within the cervical insertion instrument 120 and thereafter released. The exemplary cervical fusion implant 110, having been deposited in the disc space, effects spinal fusion over time as the natural bone healing process integrates and binds the implant with the adjacent vertebral bodies. This fusion may be facilitated or augmented by introducing or positioning various materials in a space created within or adjacent to the cervical fusion implant 110. Those materials may be introduced before, during, or after the insertion of the exemplary cervical fusion implant 110. The additional material may include bone autograft harvested from the patient receiving the spinal fusion implant 10, one or more additional bone allograft, bio-resorbables or xenograft implants, any number of non-bone implants, and any number of fusion promoting compounds such as bone morphogenic protein.

FIGS. 11-14 depict various embodiments of the exemplary cervical fusion implant 110. Some common attributes are shared among the various embodiments. More specifically, each cervical fusion implant 110 has a top surface 31, a bottom surface 33, lateral sides 14, a proximal side 22, and a distal side 16. In one embodiment, the top and bottom surfaces 31, 33 are generally parallel. It can be appreciated by one skilled in the art that although the surfaces are generally parallel, that the top 31 and bottom 33 surfaces may be angled with respect to one another to match the natural curve of the spine (i.e. lordosis or kyphosis). By way of example, implants for the cervical or lumbar regions of the spine will have anterior height greater than the posterior height to match the natural lordosis in those regions. Inversely, the implants designed for implantation into the thoracic region will be manufactured with a posterior height greater than the anterior height to match the natural kyophosis in that region. Additionally, the angled surface can aid in overall fit within the vertebral disc space.

The cervical fusion implant 110 preferably includes two receiving apertures 12 which are centrally aligned on the proximal side 22. The receiving apertures 12 extend inwardly from the proximal side 22 in a generally perpendicular fashion relative to the proximal side 22. Although shown as having a generally circular cross-section, it will be appreciated that the receiving aperture 12 may be provided having any number of suitable shapes or cross-sections, including but not limited to rectangular or triangular.

The exemplary cervical fusion implant 110 also preferably includes anti-migration features such as anti-migration teeth 6 along the top surface 31 and bottom surface 33. Additional anti-migration features may include a plurality of proximal anti-migration spikes 68 and/or distal anti-migration spikes 70 integrated vertically through the cervical fusion implant 110. The anti-migration features increase the friction between the cervical fusion implant 110 and the adjacent contacting surfaces of the vertebral bodies. That friction prohibits migration of the cervical fusion implant 110 during the propagation of natural bony fusion. It should be appreciated by one skilled in the art that such anti-migration teeth 6 can be oriented in any manner other than generally vertically (as shown) without departing from the scope of the present invention. Moreover, as described above, the spikes 68, 70 may be constructed from any of a variety of radiopaque materials, including but not limited to a metal, ceramic, and/or polymer material. When the spike elements 68, 70 are provided having such radiodense characteristics, and the implant 110 is manufactured from a radiolucent material (such as, by way of example only, PEEK and/or PEKK), the spike elements 68, 70 will be readily observable under X-ray or fluoroscopy such that a surgeon may track the progress of the implant 110 during implantation and/or the placement of the implant 110 after implantation.

The cervical fusion implant 110 has one large fusion aperture 2, extending in a vertical fashion through the top surface 31 and bottom surface 33 which will function primarily as the avenue for bony fusion between adjacent vertebrae. The cervical fusion implant 110 may have a plurality of visualization apertures 4 which can also serve as an avenue of bony fusion on the lateral sides 14 via cell migration or additional adjuvants. The visualization apertures 4 serve an additional function of allowing a clinician to make visual observations of the degree of bony fusion un-obscured by the lateral side 14 to facilitate further diagnosis and treatment.

Figure 15:
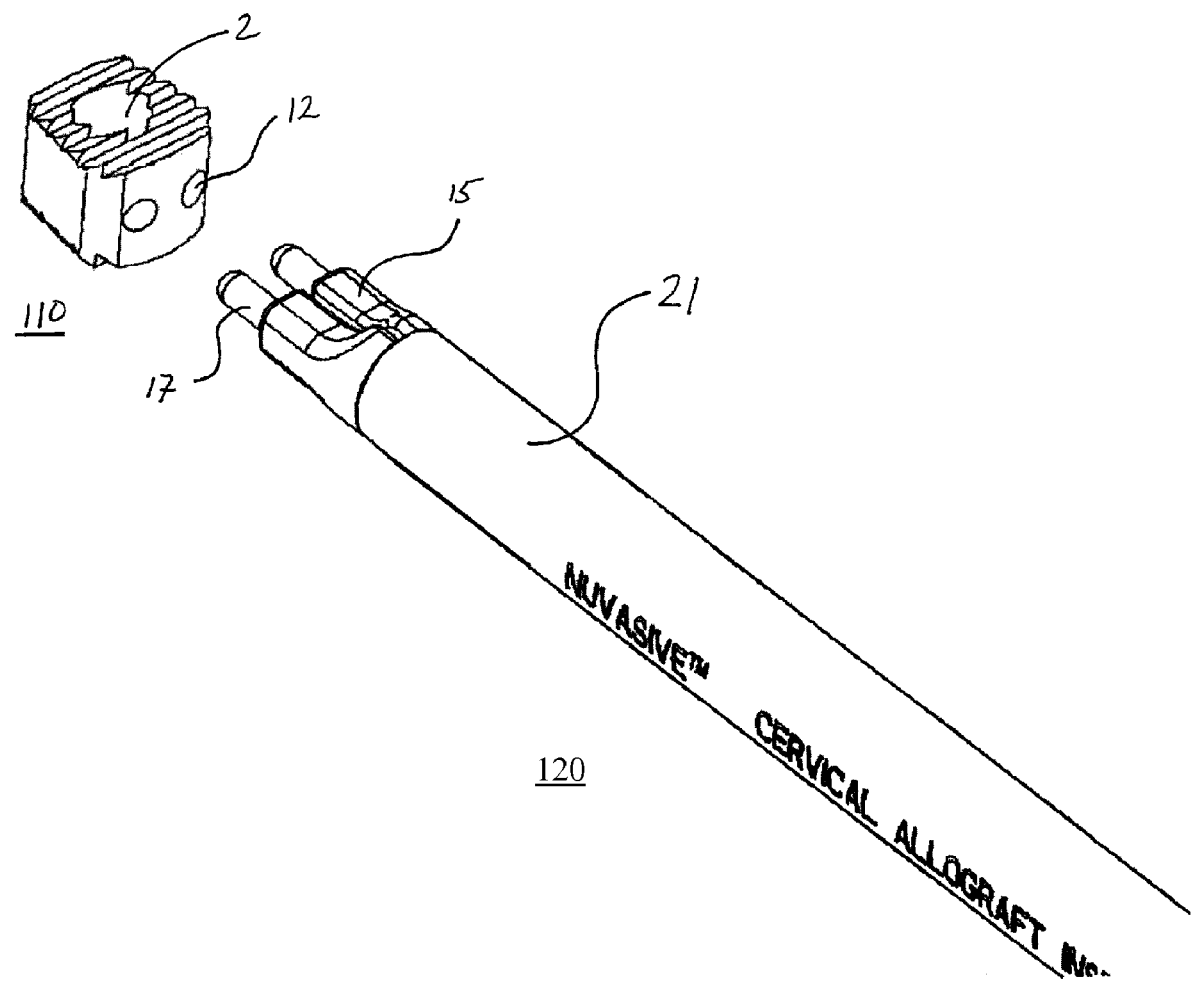
FIG. 15 is a perspective view of the cervical fusion implant of the present invention just prior to attachment to the cervical insertion device according to one embodiment of the present invention.

FIG. 15 illustrates, by way of example, the orientation of the cervical fusion implant 110 prior to attachment to the cervical insertion instrument 120 by a clinician. One skilled in the art would appreciate that although the current embodiment shows a slidable engagement, various other methods of engagement are contemplated; such as, threadable or hooking features.

Figure 16:
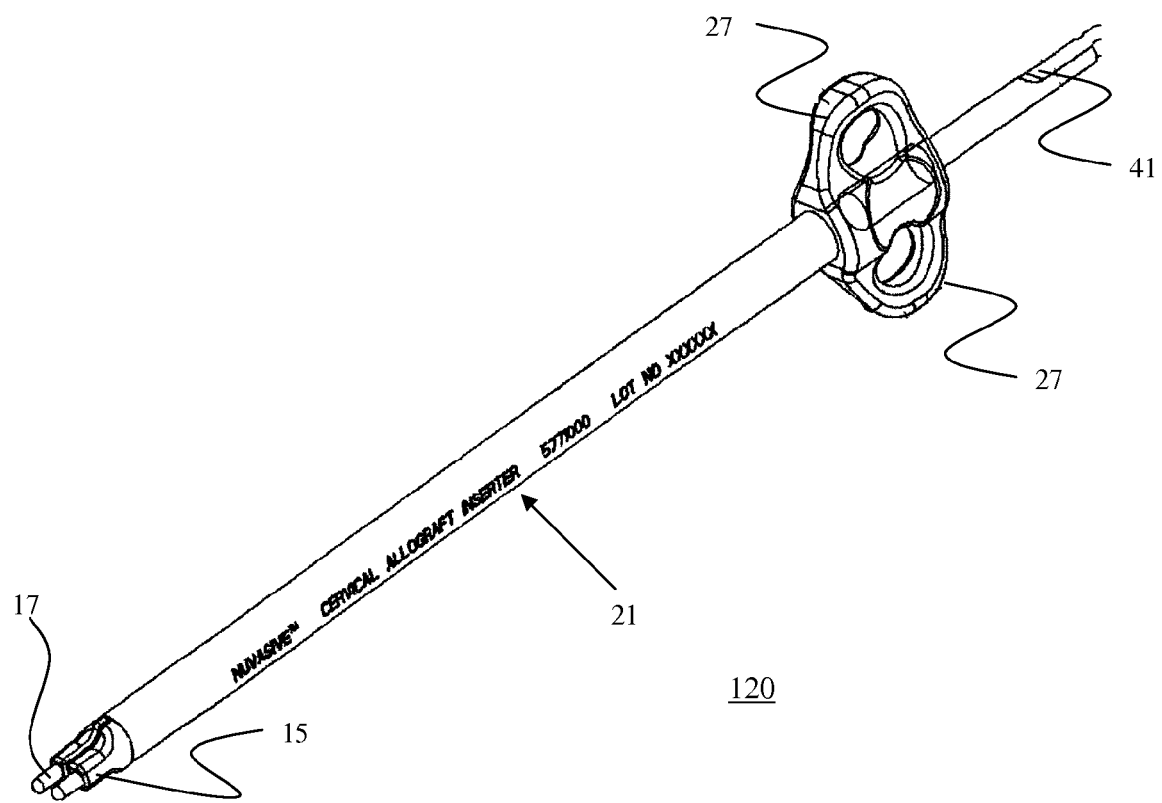
FIG. 16 is a perspective view of the insertion instrument of FIG. 10 in a fully assembled form according to one embodiment of the present invention.
Figure 17:
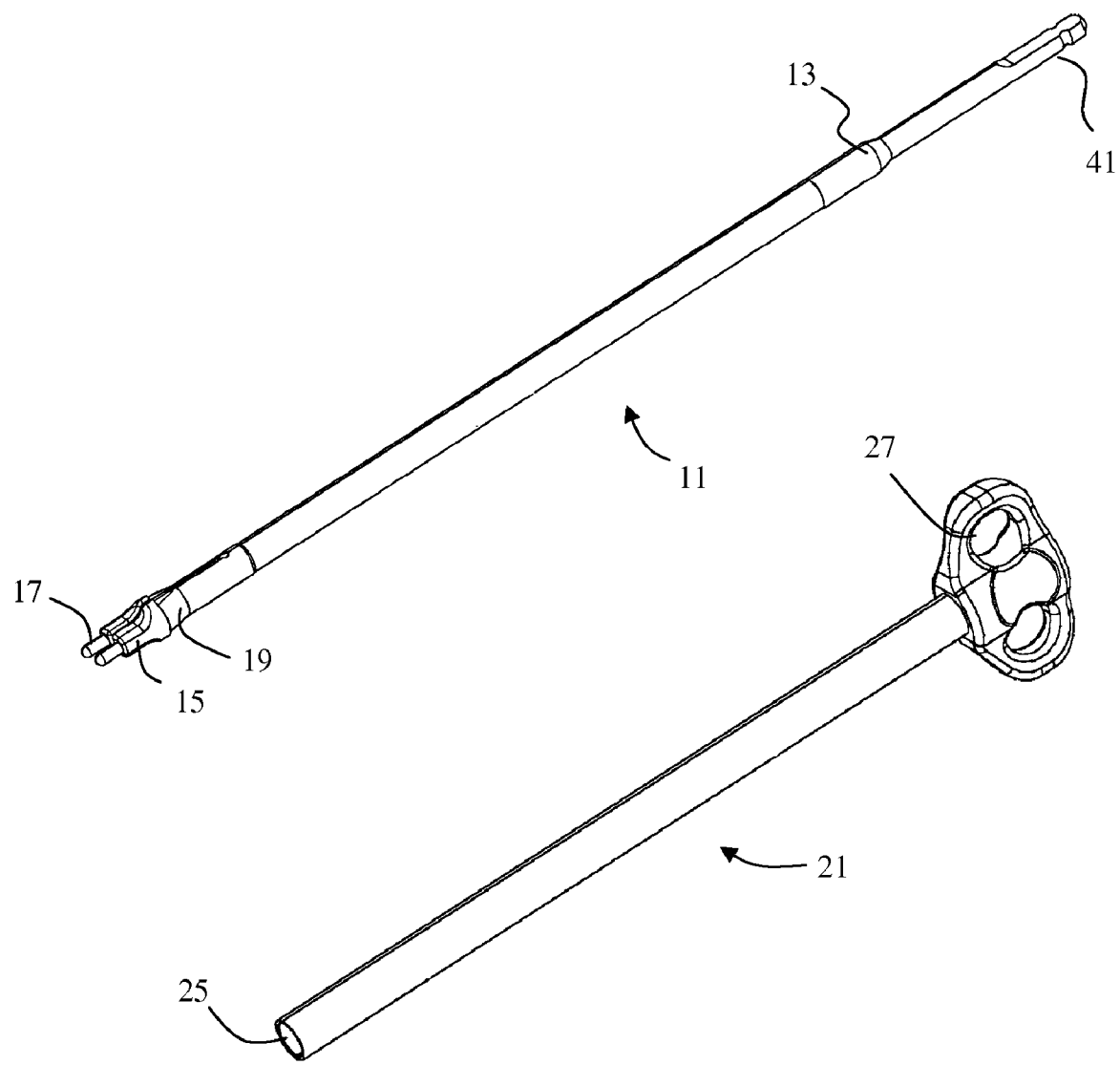
FIG. 17 is a perspective exploded view of the insertion instrument of FIG. 10, illustrating the component parts of the insertion instrument according to one embodiment of the present invention.

FIGS. 16-17 detail the tubular lock member 21 of the exemplary cervical inserter instrument 110. The tubular lock member 21 includes a central bore 25 dimensioned to receive the proximal end of the elongate fork member 11 therein. The internal dimension of the central bore 25 is smaller than the largest freestanding outer dimension of the taper feature 19. As a result, the portion of the elongate fork member 11 that may be received by the central bore 25 of the tubular lock member 21 is limited by interference between the distal end of the tubular lock member 21 and the taper feature 19 of the elongate fork member 11. In the present embodiment, the outer dimension of the threaded feature 13 of the elongate fork member 11 is smaller than the largest outer dimension of the taper feature 19 on the elongate fork member 11. A thread feature 23 (not shown) at the proximal end of the tubular lock member 21 is situated inside the central bore 25. The thread feature 23 matches the thread feature 13 on the elongate fork member 11 so that they can be threadably attached to one another. To ease the rotation of the tubular lock member 21 by hand, two semi-circular wings 27 may be provided protruding laterally outward from either side of the tubular lock member 21. Alternatively, other methods of creating a gripping surface are contemplated including but not limited to knurling or facets.

A clinician can utilize the secured system in either an open or minimally invasive spinal fusion procedure. In either type of procedure, a working channel is created in a patient that reaches the targeted spinal level. After the creation of that channel, the intervertebral space would be prepared (via known instruments as described above). After preparation, the insertion instrument 120 is used to place a cervical fusion implant 110 into the prepared intervertebral space. Once the cervical fusion implant 110 is inserted into the prepared space, the implant 110 is released from the cervical insertion instrument 120 by retracting the tubular lock member 21 from the elongate fork member 11 by rotating the tubular lock member 21 with respect to the elongate fork member 11 in the opposite direction from that used to initially secure the implant 110. That motion removes the compressive force on the purchase region 39 between the apertures 12 of the cervical fusion implant 110 and allows the engagement features 17 to be slidably removed from the apertures 12. After the engagement features 17 are disengaged from the cervical fusion implant 110, the cervical inserter instrument 120 is removed from the working channel and the channel is closed. As previously mentioned, additional materials may be included in the procedure before, during or after the insertion of the cervical fusion implant 110 to aid the natural fusion of the targeted spinal level.

In order to use the system to perform a spinal fusion procedure, the clinician must first designate the appropriate implant size. After the cervical fusion implant 110 is chosen, the engagement features 17 of the elongate fork member 11 are inserted into the apertures 12 on the implant 110. At that time the cervical fusion implant 110 and elongate fork member 11 are slidably engaged with one another. Before the clinician can manipulate the combined cervical fusion implant 110 and elongated fork member 11, they must be releasably secured together. In order to secure the cervical fusion implant 110 onto the elongate fork member 11, the clinician would next employ the tubular lock member 21. The clinician would insert the proximal end of the elongate fork member 11 into the central bore 25 of the tubular lock member 21 at its distal end. The tubular lock member 21 would then be advanced over the elongate fork member 11 until the thread feature 13 of that member and the thread feature 23 of the tubular lock member 21 become engaged.

Once engaged, advancement of the tubular lock member requires rotation of the tubular lock member 21 with respect to the elongate fork member 11. Preferably, after only a small amount of engagement of the thread features the distal end of the tubular lock member 21 would contact the taper feature 19 of the elongate fork member 11. The tubular lock member 21 would be advanced creating greater interference as the distal end approaches the distal end of the taper feature 19 which has the larger outer dimension. The increasing interference would laterally displace the clamping arms 15 of the elongate fork member 11 towards each other. Since the engagement features 17 of the elongate fork member 11 were initially inserted into the apertures 12 of the exemplary cervical fusion implant 110, the displacement of the clamping arms 15 would create a compressive force on the purchase region 39 separating the apertures 12 of the exemplary cervical fusion implant 110. That compressive force allows a clinician to manipulate the system without the exemplary cervical fusion implant 110 becoming disengaged from the cervical inserter instrument 120.

Figure 18:
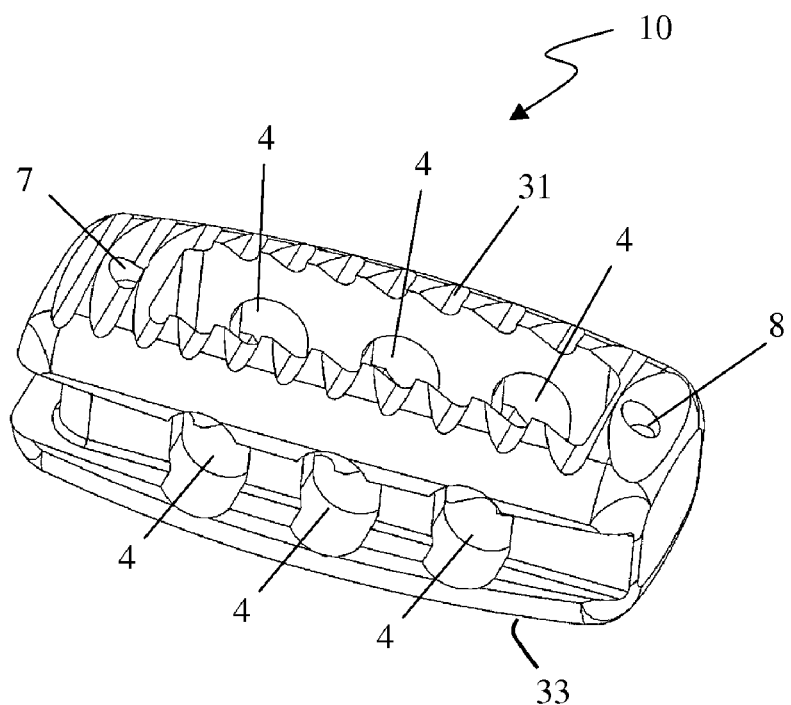
FIGS. 18 and 19 are perspective and side views, respectively, illustrating the "enhanced visualization" feature of the present invention as employed within a lumbar fusion implant according to one embodiment of the present invention.
Figure 19:
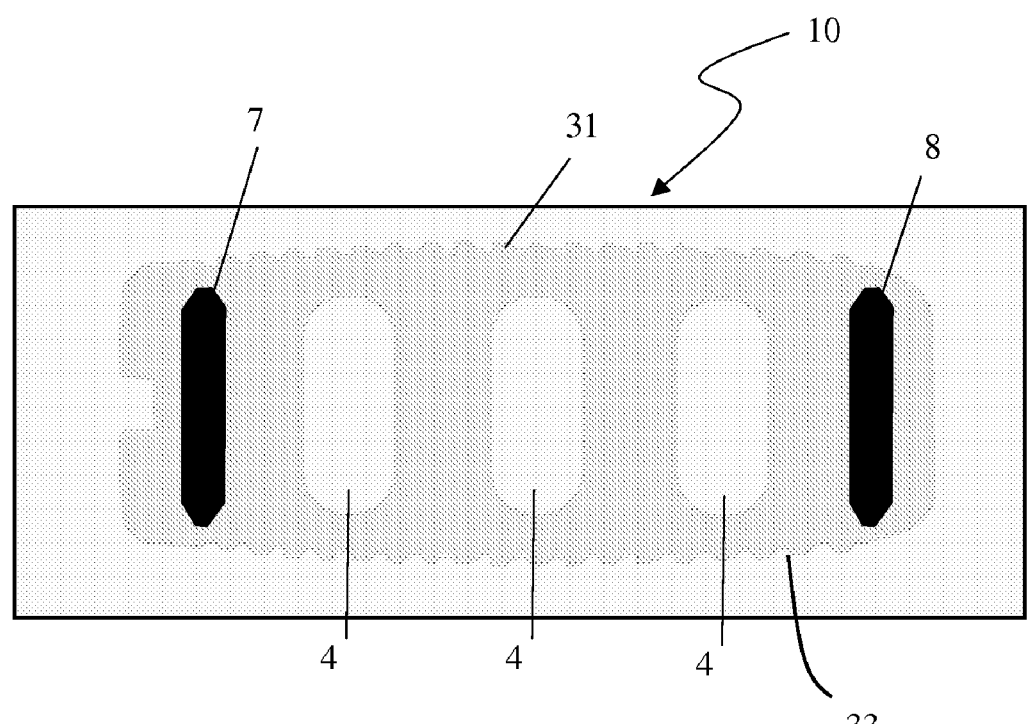
Figure 20:
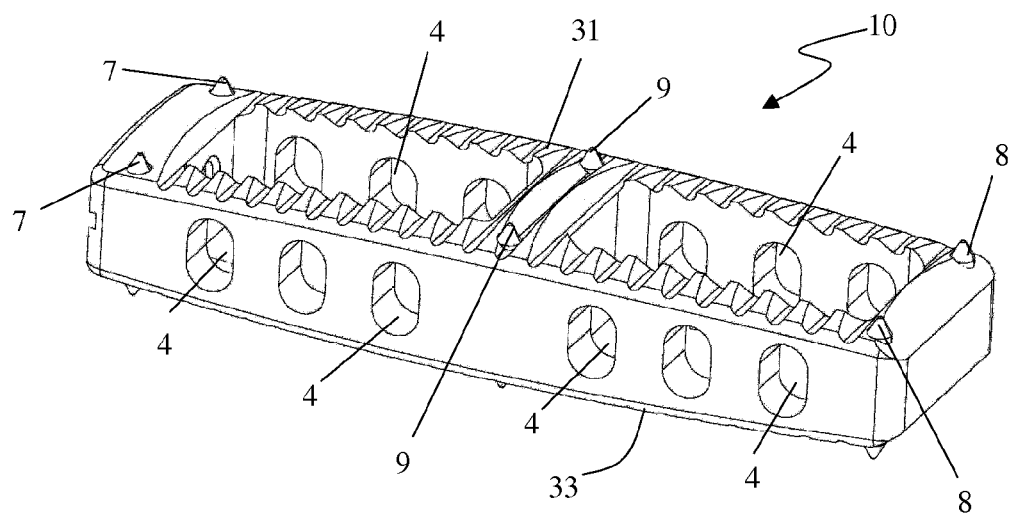
FIGS. 20 and 21 are perspective and side views, respectively, illustrating the "enhanced visualization" feature of the present invention as employed within a lumbar fusion implant according to one embodiment of the present invention.
Figure 21:
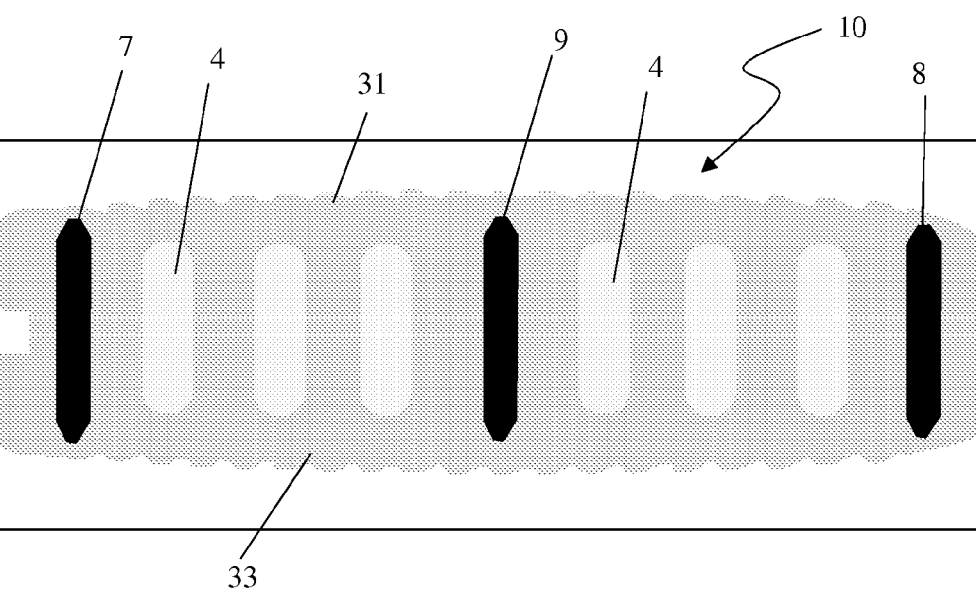
Figure 22:
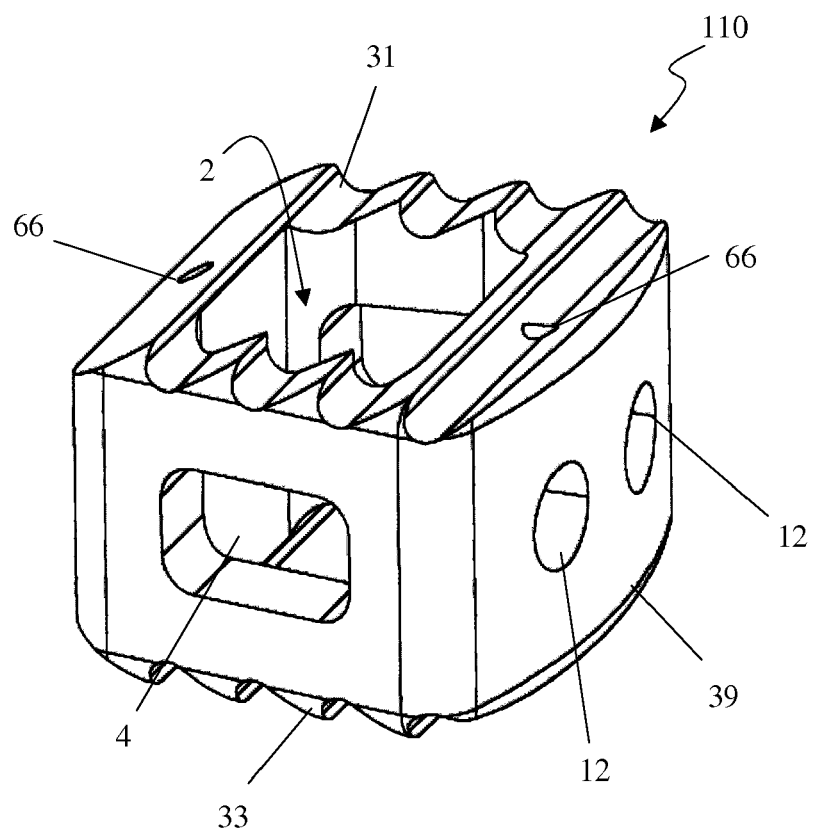
FIGS. 22 and 23 are perspective and side views, respectively, illustrating the "enhanced visualization" feature of the present invention as employed within a cervical fusion implant according to one embodiment of the present invention.
Figure 23:
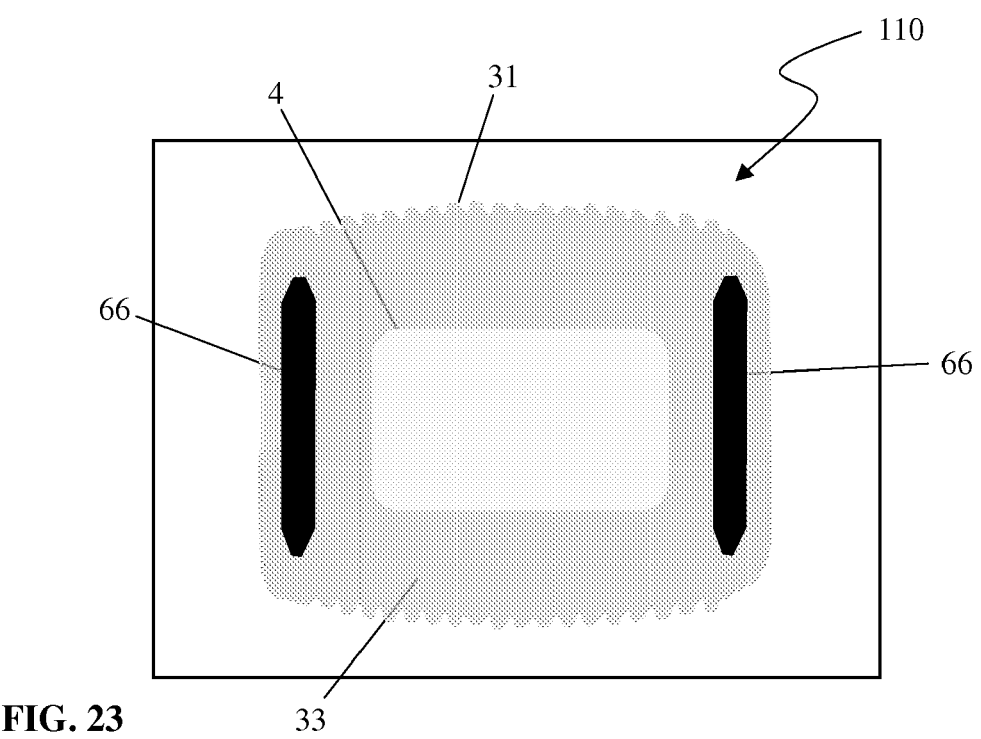

The enhanced visualization features of the implants 10, 110 are explained in greater detail with reference to FIGS. 18-23. FIG. 18 illustrates an implant 10 dimensioned particularly for use in a posterior approach (PLIF) having (by way of example only) a width ranging between 9 and 11 mm, a height ranging between 8 and 14 mm, and a length ranging between 25 and 30 mm. FIG. 19 illustrates the implant 10 of FIG. 18 from a side perspective via as taken via X-ray or fluoroscopy techniques, clearly showing the location of the spike elements 7 and 8 (there is no central spike element 9 as with FIG. 1) relative to the implant 10 and visualization apertures 4. FIG. 20 illustrates an implant 10 dimensioned particularly for use in a lateral approach (XLIF™ by NuVasive) having (by way of example only) a width of approximately 18 mm, a height ranging between 8 and 16 mm, and a length ranging between 40 and 45 mm. FIG. 21 illustrates the implant 10 of FIG. 20 from a side perspective via as taken via X-ray or fluoroscopy techniques, clearly showing the location of the spike elements 7, 8, 9 relative to the implant 10 and visualization apertures 4. FIG. 22 illustrates an implant 110 dimensioned particularly for use in the cervical spine having (by way of example only) a width of approximately 11 mm, a height ranging between 5 and 12 mm, and a length of approximately 14 mm. FIG. 23 illustrates the implant 110 of FIG. 22 from a side perspective via as taken via X-ray or fluoroscopy techniques, clearly showing the location of the spike elements 66 relative to the implant 110 and visualization apertures 4. In this fashion, a surgeon may easily track the progress of the implant 10, 110 during implantation and/or after implantation by visualizing the spike elements 7,8,9 and 66, respectively, under X-ray and/or fluoroscopy according to the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined by the appended claims.

For example, while described herein primarily with reference to the lumbar and cervical spinal surgery, it is to be readily appreciated that the spinal fusion implants of the present invention may be suitable for accomplishing fusion in the thoracic spine without departing from the scope of the present invention. Moreover, it is to be readily appreciated that the insertion tools described herein may be employed with implants of any number of suitable constructions, including but not limited to metal, ceramic, plastic or composite.

What is claimed is:

1. A spinal fusion implant of non-bone construction positionable within an interbody space between a first vertebra and a second vertebra, said implant comprising:

an upper surface including anti-migration elements to contact said first vertebra when said implant is positioned within the interbody space, a lower surface including anti-migration elements to contact said second vertebra when said implant is positioned within the interbody space, a distal wall, a proximal wall, a first sidewall and a second sidewall, said distal wall, proximal wall, first sidewall, and second sidewall comprising a radiolucent material;

wherein said implant has a longitudinal length greater than 40 mm extending from a proximal end of said proximal wall to a distal end of said distal wall;

wherein a central region of said implant includes portions of the first and second sidewalls positioned generally centrally between the proximal wall and the distal wall, at least a portion of the central region defining a maximum lateral width of said implant extending from said first sidewall to said second sidewall, wherein said longitudinal length is at least two and half times greater than said maximum lateral width;

at least a first fusion aperture extending through said upper surface and lower surface and configured to permit bone growth between the first vertebra and the second vertebra when said implant is positioned within the interbody space, said first fusion aperture having: a longitudinal aperture length extending generally parallel to the longitudinal length of said implant, and a lateral aperture width extending between said first sidewall to said second sidewall, wherein the longitudinal aperture length is greater than the lateral aperture width; and at least three radiopaque markers; wherein a first of the at least three radiopaque markers is at least partially positioned in said distal wall, a second of said at least three radiopaque markers is at least partially positioned in said proximal wall, and a third of said at least three radiopaque markers is at least partially positioned in said central region.

2. The spinal fusion implant of claim 1, further including at least one receiving aperture position is said proximal wall.

3. The spinal fusion implant of claim 2, wherein said receiving aperture is configured to releasably mate with an inserter tool.

4. The spinal fusion implant of claim 3, wherein said receiving aperture comprises a threaded receiving aperture extending into said proximal wall and having a central axis generally parallel to said longitudinal length of said implant.

5. The spinal fusion implant of claim 4, further comprising a pair of lateral grooves positioned in said proximal wall and extending laterally of said threaded receiving aperture.

6. The spinal fusion implant of claim 1, further comprising a medial support extending between the first and second sidewalls.

7. The spinal fusion implant of claim 6, wherein said medial support is positioned along said central region.

8. The spinal fusion implant of claim 1, further including a second fusion aperture extending through said upper surface and lower surface and configured to permit bone growth between the first vertebra and the second vertebra when said implant is positioned within the interbody space.

9. The spinal fusion implant of claim 8, wherein said second fusion aperture is separated from said first fusion aperture by a medial support.

10. The spinal fusion implant of claim 1, wherein said anti-migration elements of said upper surface comprise a plurality of ridges.

11. The spinal fusion implant of claim 10, wherein said plurality of ridges extend generally perpendicular to said longitudinal length.

12. The spinal fusion implant of claim 1, wherein said anti-migration elements of said upper surface comprise spike elements.

13. The spinal fusion implant of claim 12, wherein said spike elements protrude to pointed tips configured to engage said first vertebra.

14. The spinal fusion implant of claim 1, wherein at least one of said three radiopaque markers comprises an elongate body extending generally perpendicular to said longitudinal length.

15. The spinal fusion implant of claim 14, wherein aid elongate body of at least one of said three radiopaque markers is shorter than a height extending from said upper surface to said lower surface.

16. The spinal fusion implant of claim 1, further comprising a fourth radiopaque marker situated within said implant, said fourth radiopaque marker positioned in said central region at a position spaced apart from said third radiopaque marker.

17. The spinal fusion implant of claim 1, wherein said first radiopaque marker has an elongate body oriented generally perpendicular to said longitudinal length and extending entirely through a height of said distal wall, and wherein said second radiopaque marker has an elongate body oriented generally perpendicular to said longitudinal length and entirely through a height of said proximal wall.

18. The spinal fusion implant of claim 1, wherein said maximum lateral width of said implant is approximately 18 mm.

19. The spinal fusion implant of claim 1, wherein said radiolucent material comprises PEEK.

20. The spinal fusion implant of claim 1, wherein said implant includes at least one visualization aperture extending through at least one of said first sidewall and said second sidewall.

21. The spinal fusion implant of claim 1, wherein said upper and lower surfaces are generally parallel to one another.

22. The spinal fusion implant of claim 1, wherein said upper and lower surfaces are generally angled relative to one another to approximately correspond to lordosis of a lumbar spine when said implant is positioned within the interbody space.

23. The spinal fusion implant of claim 1, wherein said first fusion aperture is one of generally rectangular and generally oblong in shape.

24. The spinal fusion implant of claim 1, wherein said maximum lateral width of said implant is greater than a lateral width of the distal end of said distal wall and is greater than a lateral width of the proximal end of said proximal wall.

25. The spinal fusion implant of claim 1, wherein said implant has a height extending from said upper surface to said lower surface, wherein said maximum lateral width is greater than said height.

26. The spinal fusion implant of claim 1, wherein said central region includes a maximum height of said implant extending from said upper surface to said lower surface, wherein said maximum height is greater than a height of said distal wall and is greater than a height of said proximal wall.

27. The spinal fusion implant of claim 1, wherein the lateral aperture width of said first fusion aperture is more than two time greater than a lateral thickness of said first sidewall and is more than two time greater than a lateral thickness of said second sidewall.

28. The spinal fusion implant of claim 1, further comprising an osteoinductive material positioned with said first fusion aperture.

* * * * *

UNITED STATES PATENT AND TRADEMARK OFFICE
CERTIFICATE OF CORRECTION

| | | |
|---|---|---|
| PATENT NO. | : 8,187,334 B2 | Page 1 of 1 |
| APPLICATION NO. | : 13/079645 | |
| DATED | : May 29, 2012 | |
| INVENTOR(S) | : Matthew Curran and Mark Peterson | |

It is certified that error appears in the above-identified patent and that said Letters Patent is hereby corrected as shown below:

Column 13, Line 46 (Claim 15), delete "aid" and insert -- said --, therefor.

Signed and Sealed this
Seventh Day of August, 2012

David J. Kappos
*Director of the United States Patent and Trademark Office*

UNITED STATES PATENT AND TRADEMARK OFFICE
Certificate

Patent No. 8,187,334 B2                                                                           Patented: May 29, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Matthew Curran, Carlsbad, CA (US); Mark Peterson, Medford, OR (US); and Luiz Pimenta, Sao Paulo (BR).

Signed and Sealed this Eighteenth Day of June 2013.

<div align="right">
EDUARDO C. ROBERT<br>
<i>Supervisory Patent Examiner</i><br>
Art Unit 3733<br>
Technology Center 3700
</div>

(12) INTER PARTES REVIEW CERTIFICATE (858th)
United States Patent (10) Number: US 8,187,334 K1
Curran et al. (45) Certificate Issued: Feb. 22, 2018

(54) SYSTEM AND METHODS FOR SPINAL FUSION

(75) Inventors: Matthew Curran; Mark Peterson; Luiz Pimenta

(73) Assignee: NUVASIVE, INC.

Trial Numbers:

IPR2013-00507 filed Aug. 14, 2013
IPR2013-00508 filed Aug. 14, 2013

Inter Partes Review Certificate for:

Patent No.: 8,187,334
Issued: May 29, 2012
Appl. No.: 13/079,645
Filed: Apr. 4, 2011

The results of IPR2013-00507 and IPR2013-00508 are reflected in this inter partes review certificate under 35 U.S.C. 318(b).

INTER PARTES REVIEW CERTIFICATE
U.S. Patent 8,187,334 K1
Trial No. IPR2013-00507
Certificate Issued Feb. 22, 2018

AS A RESULT OF THE INTER PARTES REVIEW PROCEEDING, IT HAS BEEN DETERMINED THAT:

Claim 18 is found patentable.

Claims 1-5, 10, 11, 14, 15 and 19-28 are cancelled.

\* \* \* \* \*

(12) INTER PARTES REVIEW CERTIFICATE (2831st)
United States Patent
Curran et al.

(10) Number: US 8,187,334 K2
(45) Certificate Issued: Sep. 14, 2022

(54) SYSTEM AND METHODS FOR SPINAL FUSION

(75) Inventors: Matthew Curran; Mark Peterson; Luiz Pimenta

(73) Assignee: NUVASIVE, INC.

Trial Numbers:

IPR2019-00361 filed Dec. 21, 2018
IPR2019-00546 filed Jan. 10, 2019

Inter Partes Review Certificate for:

Patent No.: 8,187,334
Issued: May 29, 2012
Appl. No.: 13/079,645
Filed: Apr. 4, 2011

The results of IPR2019-00361; and IPR2019-00546 are reflected in this inter partes review certificate under 35 U.S.C. 318(b).

INTER PARTES REVIEW CERTIFICATE
U.S. Patent 8,187,334 K2
Trial No. IPR2019-00361
Certificate Issued Sep. 14, 2022

AS A RESULT OF THE INTER PARTES REVIEW PROCEEDING, IT HAS BEEN DETERMINED THAT:

Claims 16 and 18 are found patentable.

Claims 6-9 are cancelled.

\* \* \* \* \*